United States Patent
Schaeffer et al.

(10) Patent No.: US 7,078,478 B2
(45) Date of Patent: Jul. 18, 2006

(54) INHIBITION OF THE PROLIFERATION OF CELLS OF THE MULTIPLE MYELOMA

(75) Inventors: Michael Schaeffer, Munich (DE); Michaela Schneiderbauer, Altoetting (DE); Sascha Weidler, Munich (DE); Michael Hallek, Schondorf (DE)

(73) Assignee: GSF-Forschungszentrum für Umwelt Gesundheit, GmbH, Neuherberg (DE)

( * ) Notice: Subject to any disclaimer, the term of this patent is extended or adjusted under 35 U.S.C. 154(b) by 272 days.

(21) Appl. No.: 10/194,985

(22) Filed: Jul. 12, 2002

(65) Prior Publication Data

US 2003/0105287 A1   Jun. 5, 2003

Related U.S. Application Data

(63) Continuation-in-part of application No. 09/625,225, filed on Jul. 24, 2000, now Pat. No. 6,605,703.

(30) Foreign Application Priority Data

Sep. 2, 1999  (DE) ................................ 199 41 897

(51) Int. Cl.
   *C07K 14/475*  (2006.01)
   *A61K 38/18*   (2006.01)

(52) U.S. Cl. ...................... 530/300; 530/324; 530/325; 530/326; 514/2

(58) Field of Classification Search .................... None
See application file for complete search history.

(56) References Cited

FOREIGN PATENT DOCUMENTS

WO        WO/96/09382 A1    3/1996

OTHER PUBLICATIONS

Wells, Addditivity of Mutational Effects in Proteins. Biochemistry 29:8509-8517 (1990).*
Freshney Culture of Animal Cells, A Manual of Basic Technique, Alan R. Liss, Inc., New York (1983).*
Dermer Another Anniversary for the War on Cancer. Bio/Technology vol. 12, No. 3 p. 320 (Mar. 1994).*
Murakami, M. et al. "Critical Cytoplasmic Region of the Interleukin 6 Signal Transducer gp 130 is Conserved in the Cylokine Receptor Family," *PNAS USA* Dec. 1991, pp. 11349-11353, vol. 88.

* cited by examiner

*Primary Examiner*—Marianne P. Allen
*Assistant Examiner*—Regina M. DeBerry
(74) *Attorney, Agent, or Firm*—Townsend and Townsend and Crew LLP

(57) ABSTRACT

Multiple myeloma is treated by deletion mutants of the gp130 protein of the IL-3 receptor. These mutants inhibit the binding of Hck tyrosine kinase and the growth of tumor cells, particularly myeloma cells.

6 Claims, 15 Drawing Sheets

VPSVQVFSRSESTQPLLDSEERPEDLQLVDHVDGGGDGILPR

FIG. 11

Hck binding region: VPSVQVFSRSESTQPLLDSEERPEDLQLVDHVDGGDGILPR

Peptides

P1  VPSVQVFSRSESTQPLLDSE
P2  TQPLLDSEERPEDLQLVD
P3  ERPEDLQLVDHVDGGDGILPR
P4  VPSVQVFSRSESTQP
P5  RSESTQPLLDSEERP
P6  LLDSEERPEDLQLVD
P7  EDLQLVDHVDGG
P8  HVDGGDGILPR

FIG. 12

SEQUENCE LISTING

<160> NUMBER OF SEQ ID NOS: 32

<210> SEQ ID NO 1
<211> LENGTH: 30
<212> TYPE: DNA
<213> ORGANISM: Artificial Sequence
<220> FEATURE:
<223> OTHER INFORMATION: Description of Artificial Sequence:[ ]
      universal sense primer containing an integrated XbaI site and a
      Kozak signal sequence

<400> SEQUENCE: 1
gggccctcta gaccagccat ggacaaactc                                        30

<210> SEQ ID NO 2
<211> LENGTH: 33

```
<212> TYPE: DNA
<213> ORGANISM: Artificial Sequence
<220> FEATURE:
<223> OTHER INFORMATION: Description of Artificial Sequence:truncation
      specific antisense primer t828a containing an
      integrated BamHI site

<400> SEQUENCE: 2
atctggggat ccttcatgct gactgcagtt ctg                            33

<210> SEQ ID NO 3
<211> LENGTH: 30
<212> TYPE: DNA
<213> ORGANISM: Artificial Sequence
<220> FEATURE:
<223> OTHER INFORMATION: Description of Artificial Sequence:truncation
      specific antisense primer t770a containing an
      integrated BamHI site

<400> SEQUENCE: 3
gacttggact gaggatcctt ggtgtctgta                                30

<210> SEQ ID NO 4
<211> LENGTH: 30
<212> TYPE: DNA
<213> ORGANISM: Artificial Sequence
<220> FEATURE:
<223> OTHER INFORMATION: Description of Artificial Sequence:truncation
      specific antisense primer t722a containing an
      integrated BamHI site

<400> SEQUENCE: 4
actgctggat ccttcagtat taatttttc                                 30

<210> SEQ ID NO 5
<211> LENGTH: 33
<212> TYPE: DNA
<213> ORGANISM: Artificial Sequence
<220> FEATURE:
<223> OTHER INFORMATION: Description of Artificial Sequence:truncation
      specific antisense primer t702a containing an
      integrated BamHI site

<400> SEQUENCE: 5
ttctggggat cccttttttgt catttgcttc tat                           33

<210> SEQ ID NO 6
<211> LENGTH: 30
<212> TYPE: DNA
<213> ORGANISM: Artificial Sequence
<220> FEATURE:
<223> OTHER INFORMATION: Description of Artificial Sequence:truncation
      specific antisense primer t685a containing an
      integrated BamHI site

<400> SEQUENCE: 6
ggcaatatga ctggatccag gatctggaac                                30

<210> SEQ ID NO 7
<211> LENGTH: 36
<212> TYPE: DNA
<213> ORGANISM: Artificial Sequence
<220> FEATURE:
<223> OTHER INFORMATION: Description of Artificial Sequence:truncation
      specific antisense primer t650a containing an
      integrated BamHI site

<400> SEQUENCE: 7
```

```
atctggaaca ttagggatc cgtgtttttt aattag                              36
```

<210> SEQ ID NO 8
<211> LENGTH: 36
<212> TYPE: DNA
<213> ORGANISM: Artificial Sequence
<220> FEATURE:
<223> OTHER INFORMATION: Description of Artificial Sequence:partially
      complementary internal primer delta681-721s

<400> SEQUENCE: 8

```
cacaatttta attcaaaagg acacagcagt ggtatt                             36
```

<210> SEQ ID NO 9
<211> LENGTH: 36
<212> TYPE: DNA
<213> ORGANISM: Artificial Sequence
<220> FEATURE:
<223> OTHER INFORMATION: Description of Artificial Sequence:partially
      complementary internal primer delta681-721a

<400> SEQUENCE: 9

```
aataccactg ctgtgtcctt ttgaattaaa attgtg                             36
```

<210> SEQ ID NO 10
<211> LENGTH: 36
<212> TYPE: DNA
<213> ORGANISM: Artificial Sequence
<220> FEATURE:
<223> OTHER INFORMATION: Description of Artificial Sequence:partially
      complementary internal primer delta771-827s

<400> SEQUENCE: 10

```
agtggctaca gacaccaaat ttcacatttt gaaagg                             36
```

<210> SEQ ID NO 11
<211> LENGTH: 36
<212> TYPE: DNA
<213> ORGANISM: Artificial Sequence
<220> FEATURE:
<223> OTHER INFORMATION: Description of Artificial Sequence:partially
      complementary internal primer delta771-827a

<400> SEQUENCE: 11

```
cctttcaaaa tgtgaaattt ggtgtctgta gccact                             36
```

<210> SEQ ID NO 12
<211> LENGTH: 36
<212> TYPE: DNA
<213> ORGANISM: Artificial Sequence
<220> FEATURE:
<223> OTHER INFORMATION: Description of Artificial Sequence:partially
      complementary internal primer delta771-811s

<400> SEQUENCE: 12

```
agtggctaca gacaccaaca acagtacttc aaacag                             36
```

<210> SEQ ID NO 13
<211> LENGTH: 36
<212> TYPE: DNA
<213> ORGANISM: Artificial Sequence
<220> FEATURE:
<223> OTHER INFORMATION: Description of Artificial Sequence:partially
      complementary internal primer delta771-811a

<400> SEQUENCE: 13

```
ctgtttgaag tactgttgtt ggtgtctgta gccact                             36
```

<210> SEQ ID NO 14
<211> LENGTH: 36
<212> TYPE: DNA
<213> ORGANISM: Artificial Sequence
<220> FEATURE:
<223> OTHER INFORMATION: Description of Artificial Sequence:partially complementary internal primer delta820-827s

<400> SEQUENCE: 14
tacttcaaac agaactgcat ttcacatttt gaaagg                    36

<210> SEQ ID NO 15
<211> LENGTH: 36
<212> TYPE: DNA
<213> ORGANISM: Artificial Sequence
<220> FEATURE:
<223> OTHER INFORMATION: Description of Artificial Sequence:partially complementary internal primer delta820-827a

<400> SEQUENCE: 15
cctttcaaaa tgtgaaatgc agttctgttt gaagta                    36

<210> SEQ ID NO 16
<211> LENGTH: 36
<212> TYPE: DNA
<213> ORGANISM: Artificial Sequence
<220> FEATURE:
<223> OTHER INFORMATION: Description of Artificial Sequence:partially complementary internal primer delta812-827s

<400> SEQUENCE: 16
gatggtattt tgcccaggag tcagcatgaa tccagt                    36

<210> SEQ ID NO 17
<211> LENGTH: 36
<212> TYPE: DNA
<213> ORGANISM: Artificial Sequence
<220> FEATURE:
<223> OTHER INFORMATION: Description of Artificial Sequence:partially complementary internal primer delta812-827a

<400> SEQUENCE: 17
actggattca tgctgactcc tgggcaaaat accatc                    36

<210> SEQ ID NO 18
<211> LENGTH: 36
<212> TYPE: DNA
<213> ORGANISM: Artificial Sequence
<220> FEATURE:
<223> OTHER INFORMATION: Description of Artificial Sequence:partially complementary internal primer delta812-819s

<400> SEQUENCE: 18
gatggtattt tgcccaggag tcagcatgaa tccagt                    36

<210> SEQ ID NO 19
<211> LENGTH: 36
<212> TYPE: DNA
<213> ORGANISM: Artificial Sequence
<220> FEATURE:
<223> OTHER INFORMATION: Description of Artificial Sequence:partially complementary internal primer delta812-819a

<400> SEQUENCE: 19
actggattca tgctgactcc tgggcaaaat accatc                    36

```
<210> SEQ ID NO 20
<211> LENGTH: 30
<212> TYPE: DNA
<213> ORGANISM: Artificial Sequence
<220> FEATURE:
<223> OTHER INFORMATION: Description of Artificial Sequence:5' binding
      terminal Primer Ecosfp

<400> SEQUENCE: 20
ctgaccgcta gcgaattcac ttttactacc                                            30

<210> SEQ ID NO 21
<211> LENGTH: 33
<212> TYPE: DNA
<213> ORGANISM: Artificial Sequence
<220> FEATURE:
<223> OTHER INFORMATION: Description of Artificial Sequence:3' binding
      terminal Primer Bamafp

<400> SEQUENCE: 21
ggtaccgagc tcggatccct gaggcatgta gcc                                        33

<210> SEQ ID NO 22
<211> LENGTH: 5
<212> TYPE: PRT
<213> ORGANISM: Artificial Sequence
<220> FEATURE:
<223> OTHER INFORMATION: Description of Artificial Sequence:region of
      interest within acidic putative Hck binding domain

<400> SEQUENCE: 22

Ser Thr Gln Pro Leu
 1               5

<210> SEQ ID NO 23
<211> LENGTH: 7
<212> TYPE: PRT
<213> ORGANISM: Artificial Sequence
<220> FEATURE:
<223> OTHER INFORMATION: Description of Artificial Sequence:region of
      interest within acidic putative Hck binding domain

<400> SEQUENCE: 23

Ser Glu Glu Arg Pro Glu Asp
 1               5

<210> SEQ ID NO 24
<211> LENGTH: 41
<212> TYPE: PRT
<213> ORGANISM: Artificial Sequence
<220> FEATURE:
<223> OTHER INFORMATION: Description of Artificial Sequence:putative Hck
      binding acidic domain sequence deleted in gp130

<400> SEQUENCE: 24

Val Pro Ser Val Gln Val Phe Ser Arg Ser Glu Ser Thr Gln Pro Leu
 1               5                  10                  15

Leu Asp Ser Glu Glu Arg Pro Glu Asp Leu Gln Leu Val Asp His Val
            20                  25                  30

Asp Gly Gly Asp Gly Ile Leu Pro Arg
         35                  40

<210> SEQ ID NO 25
<211> LENGTH: 20
<212> TYPE: PRT
<213> ORGANISM: Artificial Sequence
```

<220> FEATURE:
<223> OTHER INFORMATION: Description of Artificial Sequence:P1 peptide
      subfragment of Hck binding region of gp130

<400> SEQUENCE: 25

Val Pro Ser Val Gln Val Phe Ser Arg Ser Glu Ser Thr Gln Pro Leu
 1               5                  10                  15

Leu Asp Ser Glu
            20

<210> SEQ ID NO 26
<211> LENGTH: 18
<212> TYPE: PRT
<213> ORGANISM: Artificial Sequence
<220> FEATURE:
<223> OTHER INFORMATION: Description of Artificial Sequence:P2 peptide
      subfragment of Hck binding region of gp130

<400> SEQUENCE: 26

Thr Gln Pro Leu Leu Asp Ser Glu Glu Arg Pro Glu Asp Leu Gln Leu
 1               5                  10                  15

Val Asp

<210> SEQ ID NO 27
<211> LENGTH: 21
<212> TYPE: PRT
<213> ORGANISM: Artificial Sequence
<220> FEATURE:
<223> OTHER INFORMATION: Description of Artificial Sequence:P3 peptide
      subfragment of Hck binding region of gp130

<400> SEQUENCE: 27

Glu Arg Pro Glu Asp Leu Gln Leu Val Asp His Val Asp Gly Gly Asp
 1               5                  10                  15

Gly Ile Leu Pro Arg
            20

<210> SEQ ID NO 28
<211> LENGTH: 15
<212> TYPE: PRT
<213> ORGANISM: Artificial Sequence
<220> FEATURE:
<223> OTHER INFORMATION: Description of Artificial Sequence:P4 peptide
      subfragment of Hck binding region of gp130

<400> SEQUENCE: 28

Val Pro Ser Val Gln Val Phe Ser Arg Ser Glu Ser Thr Gln Pro
 1               5                  10                  15

<210> SEQ ID NO 29
<211> LENGTH: 15
<212> TYPE: PRT
<213> ORGANISM: Artificial Sequence
<220> FEATURE:
<223> OTHER INFORMATION: Description of Artificial Sequence:P5 peptide
      subfragment of Hck binding region of gp130

<400> SEQUENCE: 29

Arg Ser Glu Ser Thr Gln Pro Leu Leu Asp Ser Glu Glu Arg Pro
 1               5                  10                  15

<210> SEQ ID NO 30
<211> LENGTH: 15
<212> TYPE: PRT
<213> ORGANISM: Artificial Sequence
<220> FEATURE:

```
<223> OTHER INFORMATION: Description of Artificial Sequence:P6 peptide
      subfragment of Hck binding region of gp130

<400> SEQUENCE: 30

Leu Leu Asp Ser Glu Glu Arg Pro Glu Asp Leu Gln Leu Val Asp
  1               5                  10                  15

<210> SEQ ID NO 31
<211> LENGTH: 12
<212> TYPE: PRT
<213> ORGANISM: Artificial Sequence
<220> FEATURE:
<223> OTHER INFORMATION: Description of Artificial Sequence:P7 peptide
      subfragment of Hck binding region of gp130

<400> SEQUENCE: 31

Glu Asp Leu Gln Leu Val Asp His Val Asp Gly Gly
  1               5                  10

<210> SEQ ID NO 32
<211> LENGTH: 11
<212> TYPE: PRT
<213> ORGANISM: Artificial Sequence
<220> FEATURE:
<223> OTHER INFORMATION: Description of Artificial Sequence:P8 peptide
      subfragment of Hck binding region of gp130

<400> SEQUENCE: 32

His Val Asp Gly Gly Asp Gly Ile Leu Pro Arg
  1               5                  10
```

INHIBITION OF THE PROLIFERATION OF CELLS OF THE MULTIPLE MYELOMA

CROSS-REFERENCE TO RELATED APPLICATION

This application is a continuation-in-part of application Ser. No. 09/625,225, filed Jul. 24, 2000, now U.S. Pat. No. 6,605,703, the contents of which are incorporated herein by reference in their entirety.

REFERENCE TO A SEQUENCE LISTING

[TO BE ADDED]

BACKGROUND AND SUMMARY OF THE INVENTION

The present invention relates to deletion mutants of the IL-6 receptor protein, particularly of the beta chain (gp130) of the IL-6 receptor protein, to DNA encoding said protein, and to RNA derived therefrom. Moreover, the invention relates to substances which specifically block the binding of gp130 to Hck as well as to pharmaceutical preparations containing said substances in an amount effective to treat multiple myeloma.

All literature citations in this specification are hereby incorporated herein by reference.

IL-6 is an important growth factor for multiple myelomas (MM). For this reason, mechanisms by which IL-6 induces cell growth have been studied. It has previously been shown that IL-6 induces the activation and tyrosine phosphorylation of Hck, a tyrosine kinase of the Src family. It has been demonstrated that in MM cell lines Hck binds to the IL-6 receptor β chain gp130. A series of gp130 deletion mutants has been constructed on the basis of a chimeric receptor comprising the extracellular portion of the erythropoietin receptor and the intracellular portion of gp130. Cloning of gp130 is described by Hibi, M., et al., "Molecular cloning and expression of an IL-6-signal transducer, gp130," *CELL,* 63:1149–1157 (Dec. 21, 1990). Surprisingly, the deletion of a region of 41 amino acids in length between residues 771 and 811 of gp130 (Δ771-811) results in complete disruption of Hck binding to gp130. A striking feature of this region is its remarkably high content of negatively charged residues; for this reason it has been also referred to as an "acidic domain". Since the Δ771-811 deletion is localized between the two STAT3 binding sites at residues tyrosine (Y) 814 and 767, point mutations have been generated at these sites; this was done to exclude any effect of Y814 or Y767 on the binding of gp130 to Hck. STAT3 activation by gp130 was not affected by the Δ771-811 mutant. Eventually, the stable transfection of receptor mutants into a growth factor-dependent pro B cell line, Baf-B03, showed that deletion Δ771-811 significantly reduced the proliferative response of cells to gp130 stimulation. In conclusion, it has been shown for the first time that Hck binds to an acidic domain of gp130 which is critical for mediating the proliferative response via growth factor-activated gp130.

Interleukin-6 is a major growth factor for MM cells in vitro and in vivo Klein, B., et al., "Interleukin-6 in human multiple myeloma," *Blood,* 85:863 (1995); Hallek, M., et al., "Multiple myeloma: increasing evidence for a multistep transformation process, " *Blood,* 91:3 (1998); Klein, B., et al., "Cytokine network in human multiple myeloma," *Hematol. Oncol. Clin. North Am.,* 6:273 (1992); Klein, B., "Cytokine, cytokine receptors, transduction signals, and oncogenes in human multiple myeloma," *Sem. Hem.,* 32:4 (1995); Kawano, M., et al., "Autodrine generation and requirement of BSF-2/IL-6 for human multiple myelomas, *Nature,* 332: 83 (1988); Zhang, X. G., et al., "Interleukin-6 is a potent myeloma-cell growth factor in patients with aggressive multiple myeloma," *Blood,* 74:11 (1989). Despite evidence for a role of IL-6 in the pathogenesis of MM little is known about the signaling mechanisms responsible for IL-6-mediated cell growth in MM.

To exert these biological effects IL-6 must bind to the IL-6 receptor (IL-6R) composed of two α-chains (IL-6Rα, 80 kDa) and two β chains (IL-6Rβ or gp130, 130 kDa). Two moieties of IL-6 and two pairs of these receptor chains form a functional hexameric IL-6R complex. Simpson, R. J., et al., "Interleukin-6: structure-function relationships," *Protein Sci,* 6:929 (1997); Somers, W., et al., "A crystal structure of interleukin 6: implications for a novel mode of receptor dimerization and signaling," *Embo J.,* 16:989 (1997); Ward, L. D., et al., "Influence of interleukin-6 (IL-6) dimerization on formation of the high affinity hexameric IL-6:receptor complex," *J. Biol. Chem.,* 271:20138 (1996). The subsequent intracellular signaling events are activated by gp130. Activation of IL-6R stimulates at least two major signal transduction pathways, the Ras/mitogen activated protein kinase (MAPK) signaling cascade (Neumann, C., et al., "Interleukin-6 induces tyrosine phosphorylation of the Ras activating protein Shc and its complex formation with Grb2 in the human multiple myeloma cell line LP-1, " *Eur. J. Immunol.,* 26:379 (1996); Ogata, A. et al., "IL-6 triggers cell growth via the Ras-dependent mitogen-activated protein kinase cascade," *J. Immunol,* 159:2212 (1997); Takahashi-Tezuka, M., et al., "Gab1 acts as an adapter molecule linking the cytokine receptor gp130 to ERK mitogen-activated protein kinase," *Mol. Cell. Biol,* 18:4109 (1998); Shi, Z. Q., et al., "The Shp-2 tyrosine phosphatase has opposite effects in mediating the activation of extracellular signal-regulated and c-Jun NH2-terminal mitogen-activated protein kinases," *J. Biol. Chem.,* 273:4904 (1998); and Boulton, T. G., et al., "Ciliary neurotrophic factor/leukemia inhibitory factor/interleukin 6/oncostatin M family of cytokines induces tyrosine phosphorylation of a common set of proteins overlapping those induced by other cytokines and growth factors," *J. Biol. Chem.,* 269:11648 (1994)) and the Janus kinase (JAK)/signal transducer and activator of transcription (STAT) pathway (Berger, L. C., et al., "Tyrosine phosphorylation of JAK-TYK kinases in malignant plasma cell lines growth-stimulated by interleukins 6 and 11, " *Biochem. Biophys. Res. Commun.,* 202:596 (1994); Ihle, J. N., et al., "Signaling by the cytokine receptor superfamily: JAKs and STATs," *Trends. Biochem. Sci.,* 19:222 (1994); Stahl, N., et al., "Association and activation of Jak-Tyk kinases by CNTF-LIF-OSM-IL-6β receptor components," *Science,* 263 (1994); Gerhartz, C., et al., "Differential activation of acute phase response factor/STAT3 and STAT1 via the cytoplasmic domain of the interleukin-6 signal transducer gp130, " *J. Biol. Chem.,* 271:12991 (1996)). However, the signaling cascades mediating IL-6 induced cell growth are not well defined. It was shown earlier that JAK and STAT proteins are activated by IL-6 in MM cells independently of the proliferative response. In contrast, MAPK was only activated in cells and cell lines showing a proliferative response to IL-6 (Ogata, A. et al., *J. Immunol.,* 159:2212 (1997), cited above).

The inventors herein have previously shown that at least three members of the Src-family of tyrosine kinases, Fyn, Hck, and Lyn, bind to gp130 in MM cells. Hallek, M., et al., "Signal transduction of interleukin-6 invlves tyrosine phosphorylation of multiple cytosolic proteins and activation of Src-family kinases Fyn, Hck, and Lyn in multiple myeoloma cell lines," *Exp. Hematol.*, 25:1367 (1997). Stimulation of cells with IL-6 increased the activity of these kinases.

It is an object of the present invention to provide means for the inhibition or at least significant reduction of the stimulation of multiple myeloma cells by IL-6 in order to at least significantly decrease the proliferation of tumor cells and particularly of mycloma cells.

The present invention provides an IL-6 receptor protein having a deletion in the region of the beta chain which at least comprises amino acids 771-811. In further studies, this region may be restricted further to reveal smaller deletion regions within the 771-811 region which inhibit the binding of Hck. Preferably, the binding of Hck to gp130 is reduced by more than 90%. It is to be understood however that a larger region of gp130 which comprises the amino acid sequence mentioned above or portions thereof may also be deleted. Preferred deletion mutants are those that comprise the region of amino acids 771-811 or portions thereof.

The present invention resides not only the IL-6 receptor protein having the above-mentioned deletion in gp130 but also in gp130 itself carrying the deletion in the region of 771-811 or portions thereof. The present invention also resides in the IL-6 receptor protein and gp130 with deletions extending beyond the 771-811 region and yet still inhibiting the interaction between Hck and gp130. The invention further resides in DNA encoding the IL-6 receptor proteins characterized above or the mutant gp130 as well as RNA derived from such DNA.

BRIEF DESCRIPTION OF THE FIGURES

FIG. 11 is a reproduction of a sequence deleted from gp130 (SEQ ID NO:24).

FIG. 12 is a diagram showing various peptide subfragments (SEQ ID NOS:25–32) of the Hck binding region of gp130 (SEQ ID NO:24) that were used for testing.

DETAILED DESCRIPTION OF THE INVENTION AND PREFERRED EMBODIMENTS

Figure 1:
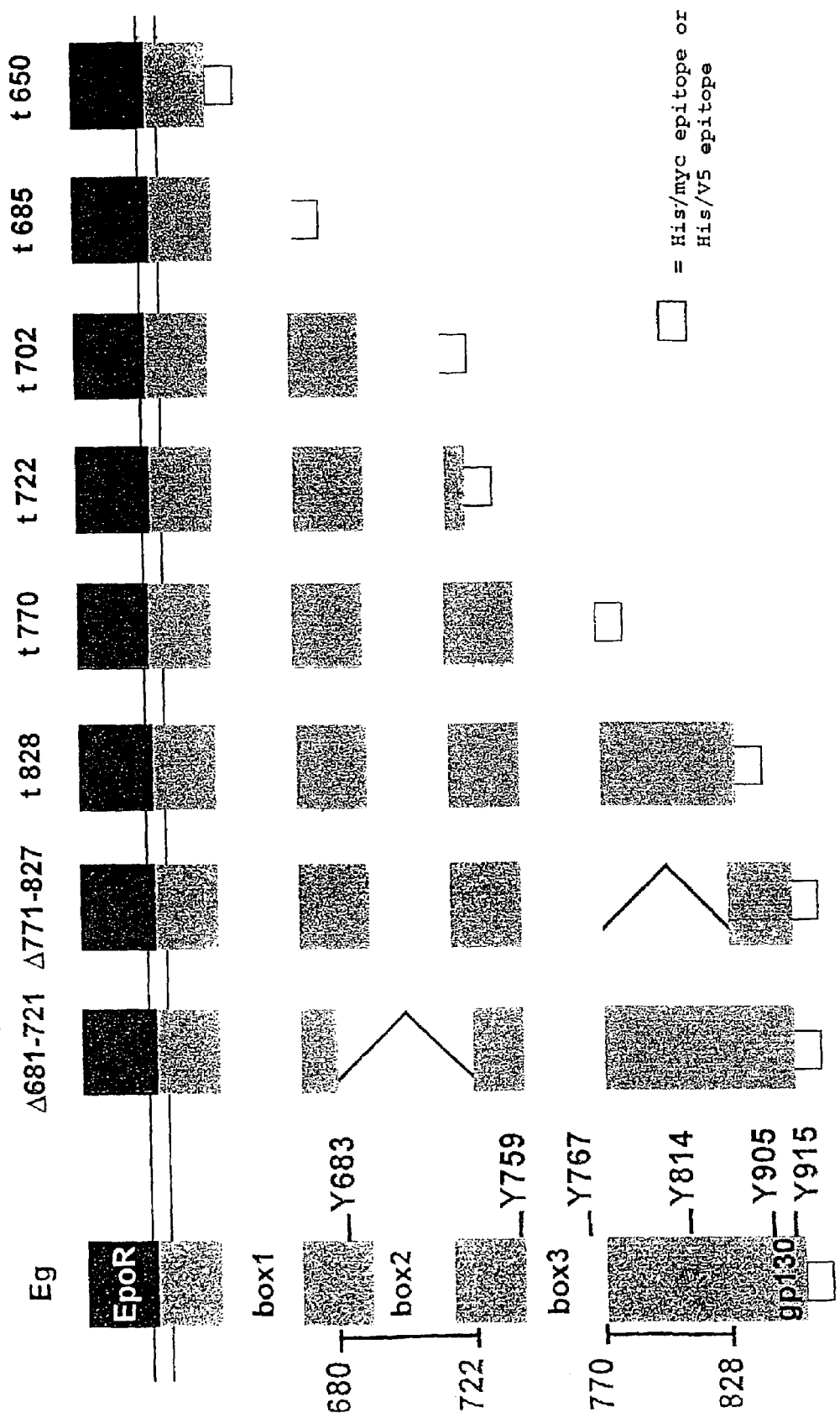
FIG. 1 is a schematic overview of gp130 truncation and deletion mutants.

A surprising discovery of this invention is that deletion of a specific region of gp130 abolishes the binding of Hck kinase. It is further surprising that this deleted region was not localized in the region of homology boxes which are known to be present in several different growth factor receptors and for which the binding of signaling proteins thereto has been shown. It is still further surprising that the deletion mutants of gp130 in the region described below exert an unexpectedly marked inhibition of myeloma cell proliferation.

The region of 41 amino acids found by the present inventors may be further restricted by conventional deletion studies. For example, receptor mutants are prepared for this purpose comprising smaller deletions in the region of amino acids 771-811. In an alternative embodiment, peptides are prepared that contain smaller regions of the above-mentioned 41-amino acid deletion region; these smaller peptides containing respective partial sequences of the Hek binding domain are used to "fish" Hck. In this manner it will be possible to find such amino acids or amino acid regions, respectively, which are required for Hek binding and thereby accelerate and simplify the so-called "drug design." In particular, two regions consisting of 5 and 7 amino acids, respectively, are of interest within the region comprising 41 amino acids, namely the regions STQPL (SEQ ID NO:22) and SEERPED (SEQ ID NO:23).

On the basis of the deletion region found according to the present invention which comprises amino acids 771-811 of the IL-6 receptor protein beta chain the skilled artisan will be able to purposefully select substances blocking the Hck tyrosine kinase binding site on gp130 protein found according to the present invention. Furthermore, substances may be purposefully found which specifically block the gp130 protein binding site on Hck tyrosine kinase. These substances may for example be proteins, preferably short peptides blocking the docking site, i.e. the protein binding pocket. Other examples are inorganic or organic molecules that are not naturally-occurring proteins.

Starting with the knowledge of the binding region of Hck to gp130 gained by this invention, one skilled in the art it will be able to develop inhibitors, such as peptides, which fit into the Hck "binding pocket" equally well as or even better than Hck and which then block this pocket for Hck, i.e., prevent or at least inhibit the intracellular protein-protein interaction, herein abbreviated as "binding," between Hck and gp130. The same object may be achieved by using synthetically prepared substances mimicking Hck or at least the binding region of Hck to gp130 without exerting its function of the promotion of tumor cell growth.

Based on the present invention and using well-known selection techniques the skilled artisan will be able to find such substances which specifically block the binding region of Hck on the beta chain of the IL-6 receptor protein. This means that the binding site for Hck on gp130 will be masked so that Hck will be unable to recognize and particularly to bind to the binding region.

In an alternative embodiment of the present invention, substances that specifically mask the binding region for gp130 on the Hck tyrosine kinase protein are selected so that Hck will be unable to recognize and particularly to bind to its native binding site on gp130.

In a further embodiment of the present invention, peptides comprising amino acids 771-811 of gp130 or portions of this region which are capable of binding to Hck tyrosine kinase are generated. These peptides may be added to myeloma cells or administered to patients in amounts that cause competitive binding to the Hck tyrosine kinase to occur whereby the native binding site of Hck on gp130 is competitively blocked so that the number of Hck molecules able to bind to gp130 will be considerably decreased at least to that extent that the proliferation of myeloma cells is inhibited.

The term "binding" according to the present invention means any type of interaction of the Hck tyrosine kinase with gp130 which is capable of performing a signal transduction between Hck and gp130. This interaction between Hck and gp130 will be avoided by the deletion mutants described above as well as the inhibitors presented herein.

The substances contemplated for use in a screening process comprise inorganic and organic molecules wherein the organic molecules are both proteins or peptides and molecules lacking amino acids.

After restricting the binding domain of Hck on gp130 to a small region using the present invention conventional screening processes may be used for a relatively quick and purposeful analysis and selection of molecules in large amounts which bear the features desired according to the present invention. Substances having the desired properties, i.e. which inhibit or at least strongly reduce the specific binding of Hck to gp130, may be processed to form a pharmaceutical preparation which together with conventional pharmaceutical carriers and additives may be used in patients suffering from a tumor, e.g. a multiple myeloma. Using this pharmaceutical preparation it will be possible to significantly inhibit the proliferative growth of tumor cells, e.g. myeloma cells, to achieve a therapeutical effect, i.e. at least an alleviation of the disease.

While it has been known that Hck interacts with gp130, however, it was new to identify the binding domain and above all to find that a deletion of this binding site results in a marked decrease of the cell growth of tumor cells. On the basis of the present invention it is now possible to purposefully develop means for the inhibition or even the abolishment of the interaction between Hck and gp130 using methods known per se.

The knowledge of the binding domain of Hck on the gp130 molecule which is highly relevant for the pathogenesis of a tumor disease has been the initial and essential step for a purposeful development of medicaments. Since the protein sequence has now been identified, data bases may be screened. For example, natural substances which may be used as the blocking agent may be found in these data bases, or the possible three-dimensional structure of the binding pocket may be deduced from the amino acid sequence by means of computer programs. Then, synthetic substances which closely fit into the binding pocket may be prepared that are directed against the pocket.

Because redundancy is often encountered in nature it may be considered that the Hck binding domain is also present in other molecules with which Hck interacts. Furthermore, the amino acid sequence described in the present invention enables screening for novel and up to now unknown binding partners of Hck. Hck belongs to the family of Src kinases. According to present knowledge this family comprises 9 kinases with high homology to each other all of which are potential or have been identified as proto-oncogenes and are highly likely to participate in the generation of numerous cancer types. On the basis of the binding domain described according to the present invention a search may be made for new binding partners of Hck.

In the following, the present invention will be described in more detail with respect to Examples and Figures. The Figures show:

FIG. 1: Schematic overview of gp130 truncation and deletion mutants. Several truncation and deletion mutants of gp130 were cloned as chimeric receptor molecules as described in the method section, the numbers indicating amino acids of wild type gp130. The sites of the tyrosine residues and the "acidic domains" are indicated. All of the mutants as well as wild type gp130 (Eg) carry His and myc labels for the expression in Cos-7 cells or His and V5 labels for Baf-B03 cell experiments.

Figure 2:
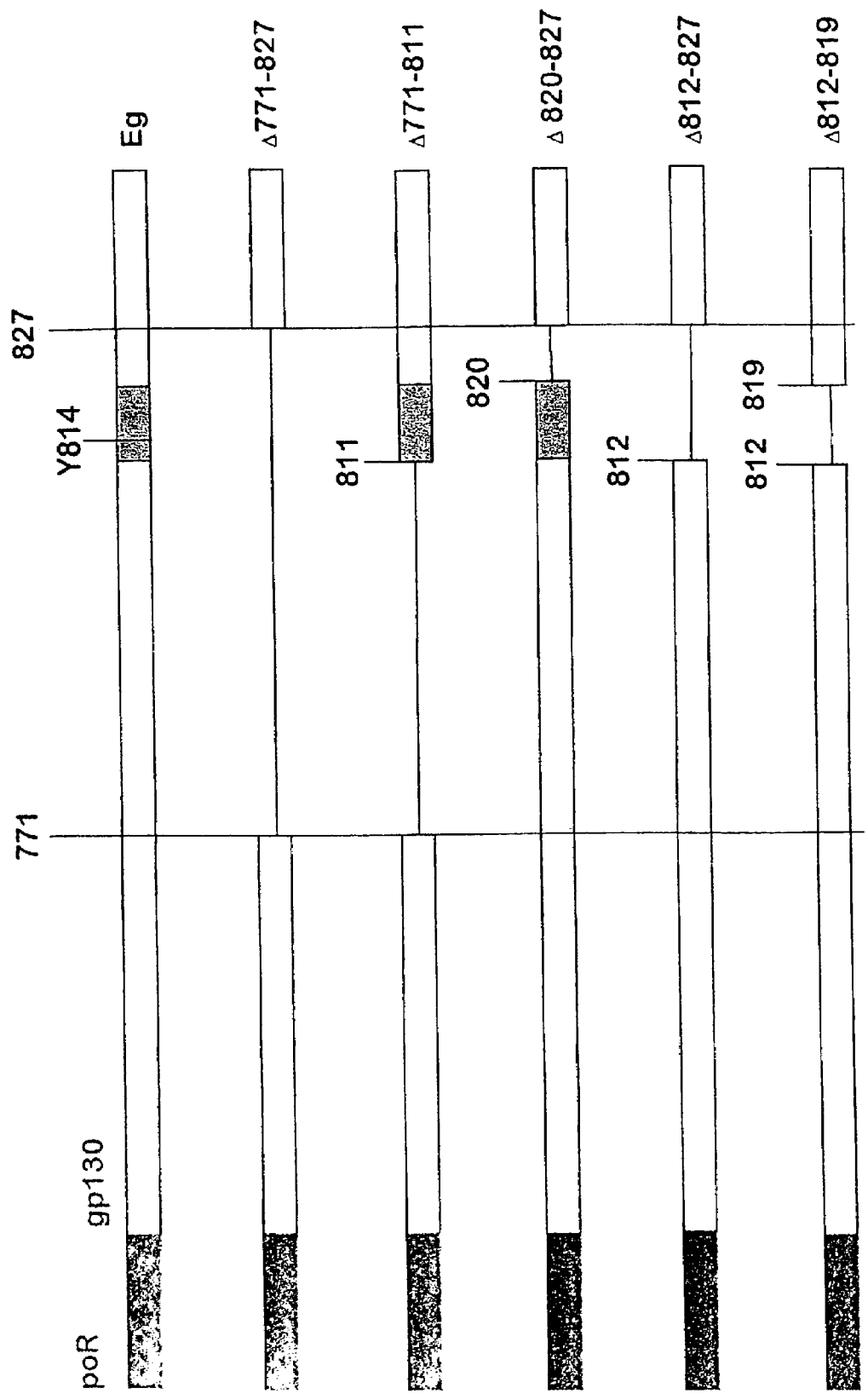
FIG. 2 is a diagram showing the internal deletions in the Hck binding region.

FIG. 2: Diagram showing internal deletions in the Hck binding region. Several chimeric gp130 mutants with further deletions in the Hck binding region (771-811) were constructed as described. The numbers represent amino acid positions in wild type gp130. The erythropoietin receptor domain has been underlaid with black, gp130 with light grey, and the STAT3 binding region at tyrosine 814 in dark grey.

Figure 3:
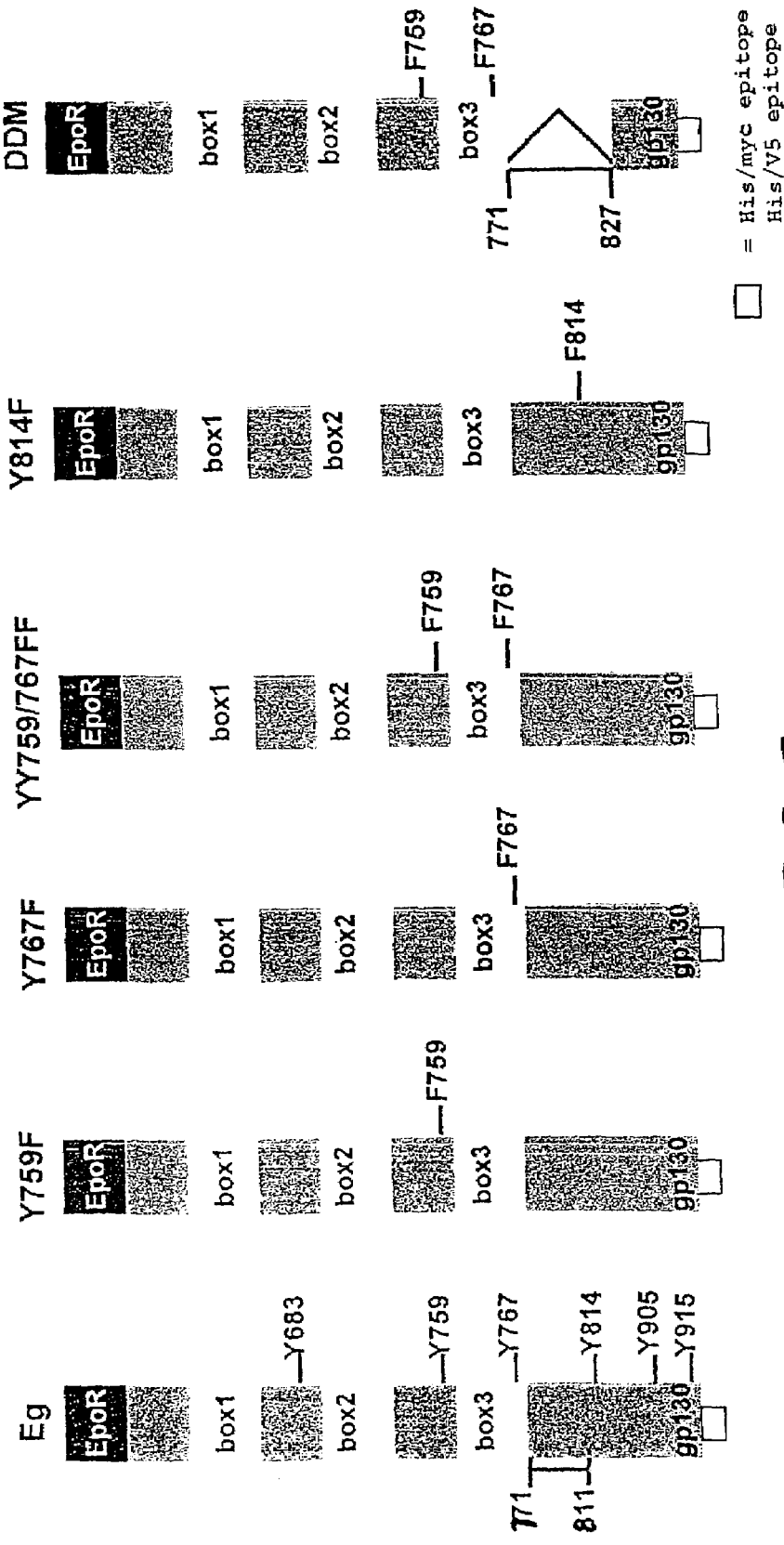
FIG. 3 is a diagram showing point mutations in gp130.

FIG. 3: Point mutations of gp130. Several site specific mutations have been introduced in gp130. The three tyrosine residues in the vicinity of the Hck binding region (771-811) were point mutated to phenylalanine (756, 767, and 814). In addition, a double point mutant (YY759/767FF) was constructed. The DDM mutant (double point and deletion mutant) lacks tyrosines 759 and 767 as well as amino acids 771-827. All of the mutants as well as wild type gp130 (Eg) carry His and myc labels for the expression in Cos-7 cells or His and V5 labels for Baf-B03 cell experiments.

Figure 4:
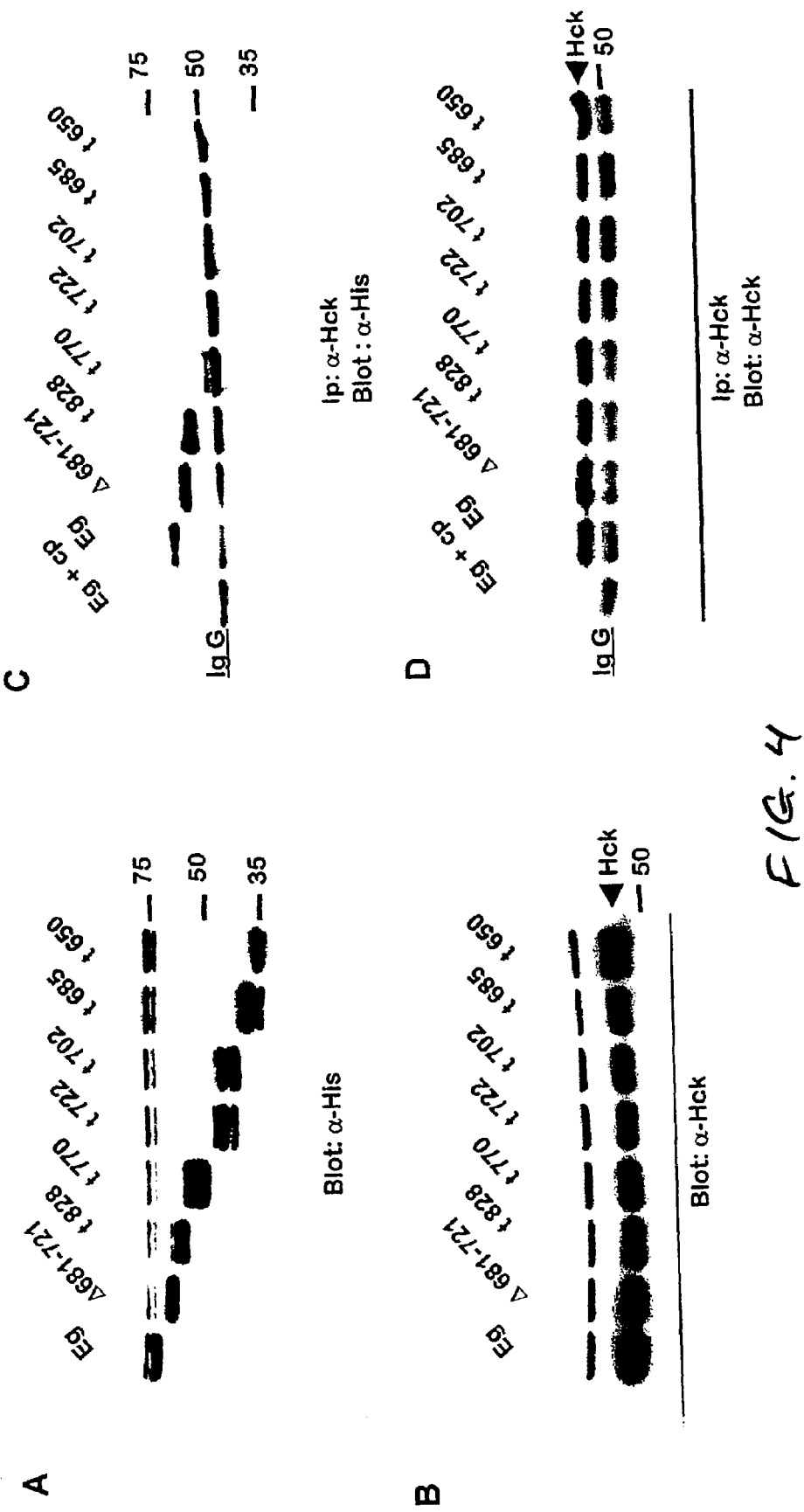
FIG. 4 is a series of Western blots showing the selective binding of Hck to gp130.

FIG. 4: Selective binding of Hck to gp130. Several gp130 mutants were expressed together with Hck cDNA in Cos-7 cells. Expression of recombinant proteins was studied by Western blotting using specific antibodies against His-label (A) or Hck (B), respectively. Binding of Hck to gp130 was investigated by immune precipitation using a Hck antibody and subsequent blotting with anti-His-label antibodies to detect the co-precipitated EPOR-gp130 fusion protein (C). Aliquots of the IP reactions were run on an additional gel and blotted with Hck antibodies to demonstrate equal precipitation of Hck (D). In lane 1 of C and D, Hck was blocked by preincubation with a specific blocking peptide. Molecular weight markers and IgG bands are as indicated. The region containing the Hck binding domain was internally deleted (Δ771-811), and co-precipitation of Hck with gp130 was investigated as above.

FIG. 5: Deletion of 41 amino acids inhibits Hck binding. A: Cos-7 cells were transfected with cDNAs for Hck and the receptor mutants indicated. Protein expression was investigated by Western blotting using anti-Hck and anti-His-label antibodies (left panel). For the immune precipitation experiments (right panel) and the mutants, Eg and t650 refer to FIGS. 1 and 4. B: The internal deletion of amino acids 771 to 827 was narrowed down to exclude the STAT3 binding site at tyrosine residue 814 of gp130. Expression of receptor mutants and Hck was studied using the appropriate antibodies (left panel). As an internal control, also lysate of normal Baf cells (Baf wt) was applied to these gels. Hck precipitates were blotted with α-His antibodies, then stripped and blotted with anti-Hck antibodies (right panel). As a control for the precipitation experiments Hck binding was blocked by preincubation of the antibody with a specific blocking peptide (right panel, lane 1). The positions of Hck and the molecular weight markers are as indicated.

Figure 6A:
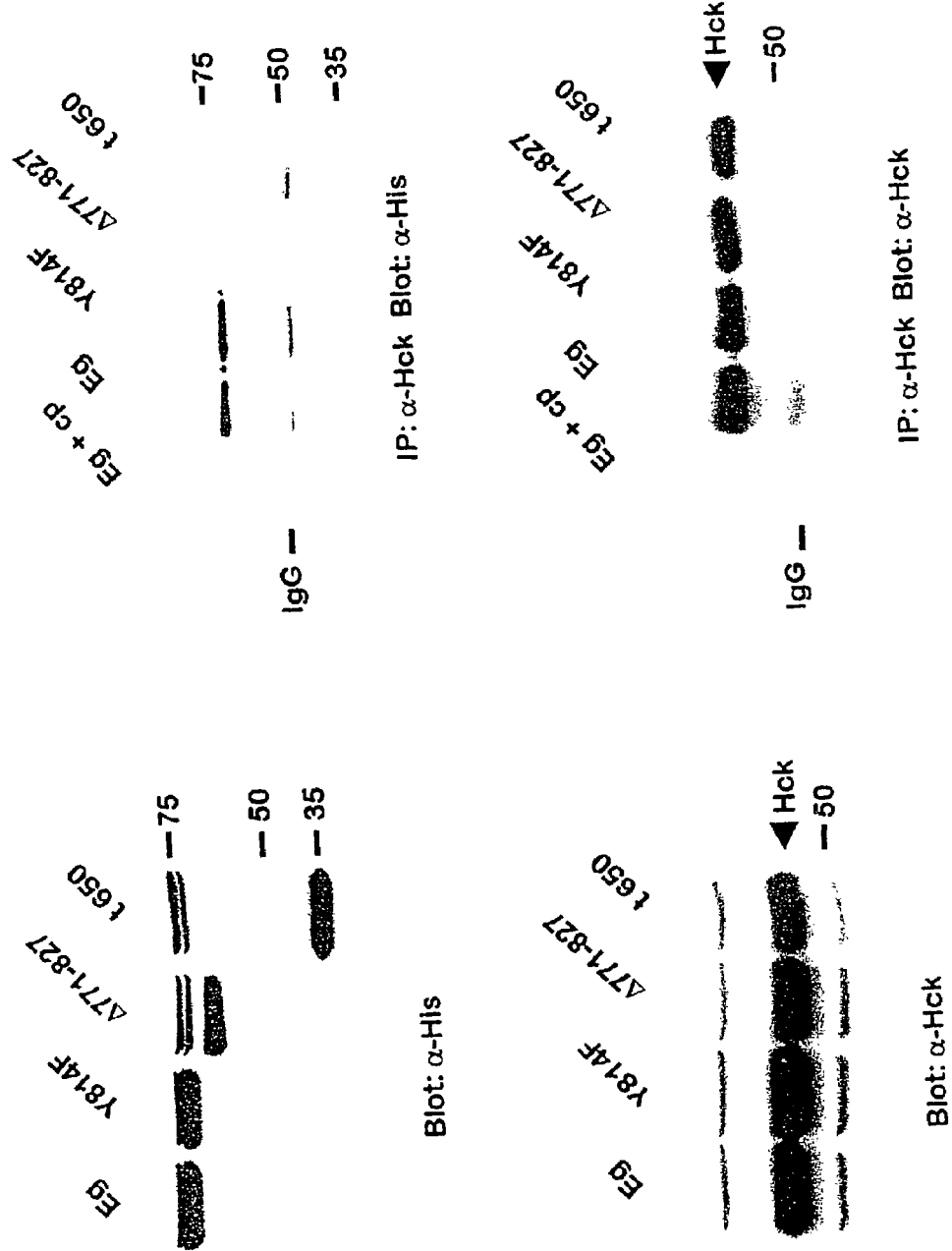
FIG. 6 is a series of Western blots showing that the binding of Hck to gp130 is independent of tyrosine residues 759, 767, and 814.
Figure 6B:
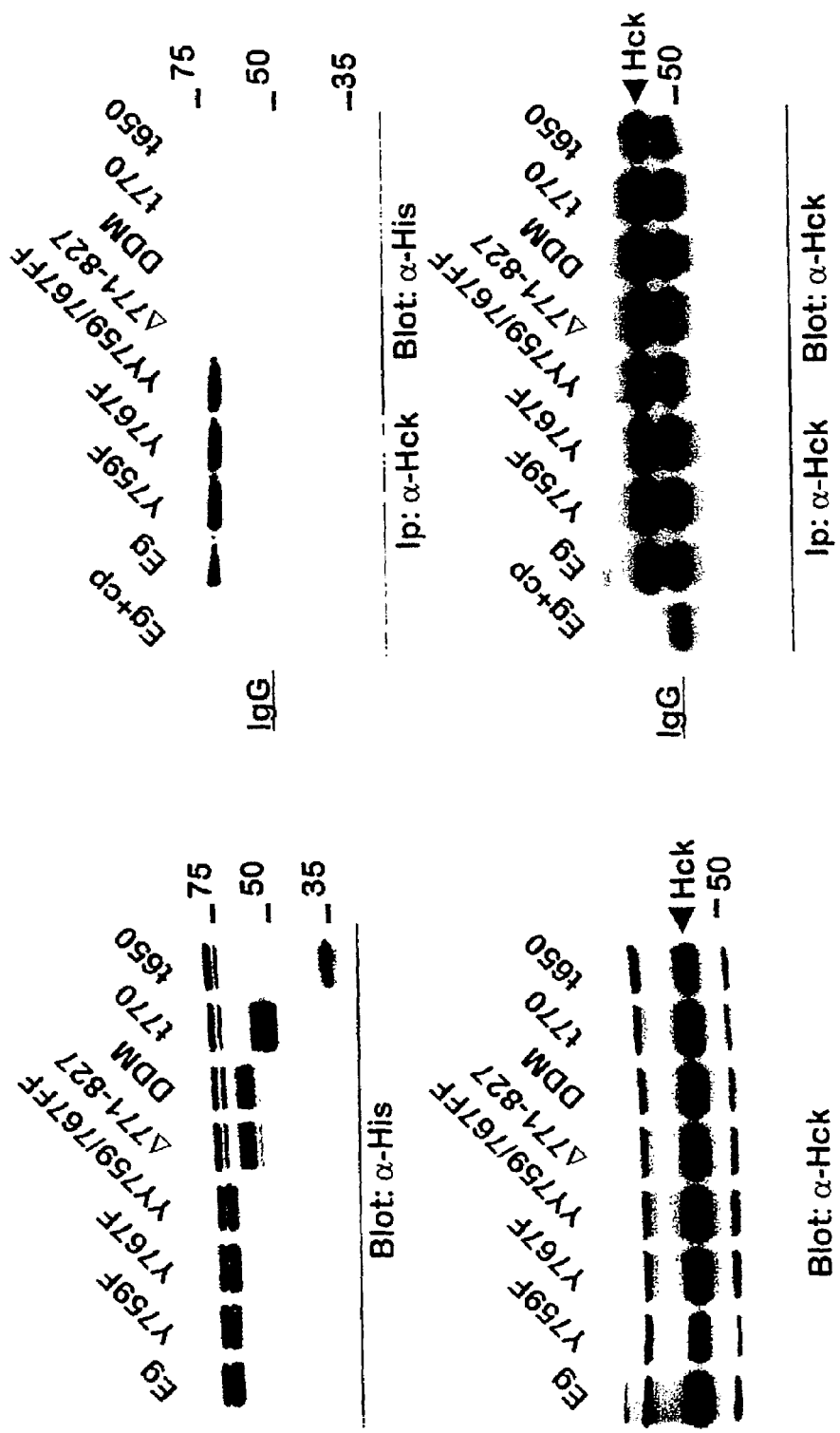

FIG. 6: Binding of Hck to gp130 is independent of tyrosine residues 759, 767, and 814. A: Cos-7 cells were transfected with cDNAs for Hck and with cDNAs for: full length EPOR-gp130 fusion protein (Eg), the point-mutated construct Y814F, the construct with the deletion of amino acids 771 to 827 (Δ771-827), and the truncated mutant (t650). The lysates were investigated for expression of recombinant proteins by blotting with a-His and a-Hck antibodies (left panel). Hck precipitates were blotted with α-His antibody, then stripped and blotted with α-Hck antibody (right panel), in addition Hck was blocked by preincubation with a specific blocking peptide (cp, lane 2, right panel). The positions of Hck and the molecular weight markers were as indicated. B: Several mutant gp130 molecules were transfected in Cos-7 cells together with Hck cDNAs. The lysates were tested for expression of the recombinant protein by blotting with α-His and α-Hck antibodies (left panel). Then, the Hck precipitates were blotted with α-His antibady. To determine the precipitation efficiency, aliquots of the precipitation reaction were blotted with α-Hck antibody (right panel). Hck was blocked by preincubation with a specific blocking peptide (cp, lane 2, right panel). The positions of Hck and the molecular weight markers were as indicated.

Figure 7:
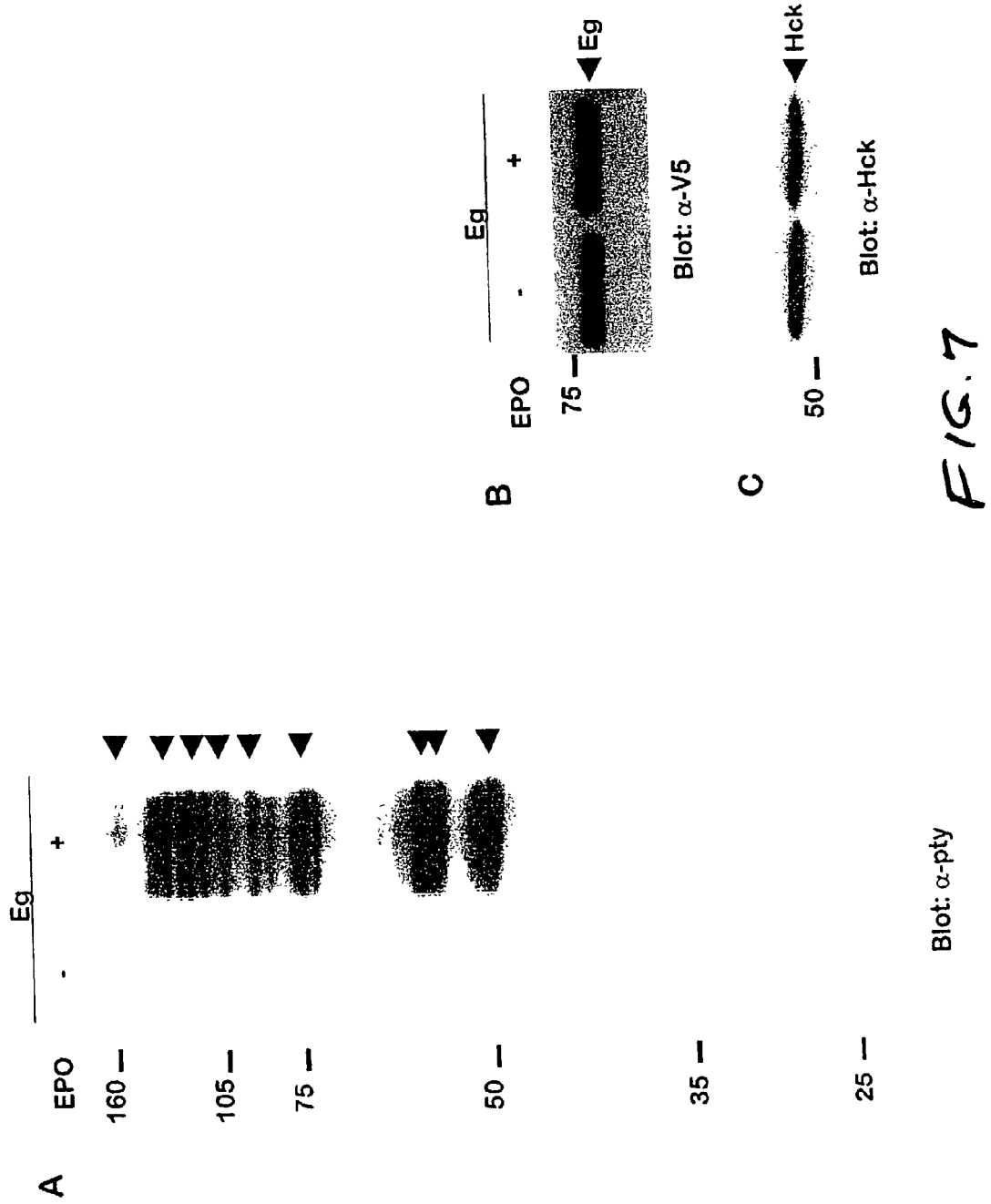
FIG. 7 is a series of blots showing that erythropoietin induces tyrosine phosphorylation of several cytoplasmic proteins in cells transfected with the chimeric receptor.

FIG. 7: Erythropoietin induces tyrosine phosphorylation of several cytoplasmic proteins in cells transfected with the chimeric receptor. Baf-B03 cells were transfected with expression vectors for Hck and Eg. Lysates of these cells were stimulated with either 80 U/ml EPO(+) or with medium alone (−) for the times indicated. Following separation on a 10% SDS page the EPO-induced tyrosine phosphorylation was studied by blotting with anti-phosphotyrosine antibody PY 99 (A). Expression of Eg (B) and Hck (C) were investigated following stripping and reblotting with the appropriate antibodies. The positions of significantly phosphorylated proteins are indicated by arrows. Molecular weight markers are shown.

Figure 8:
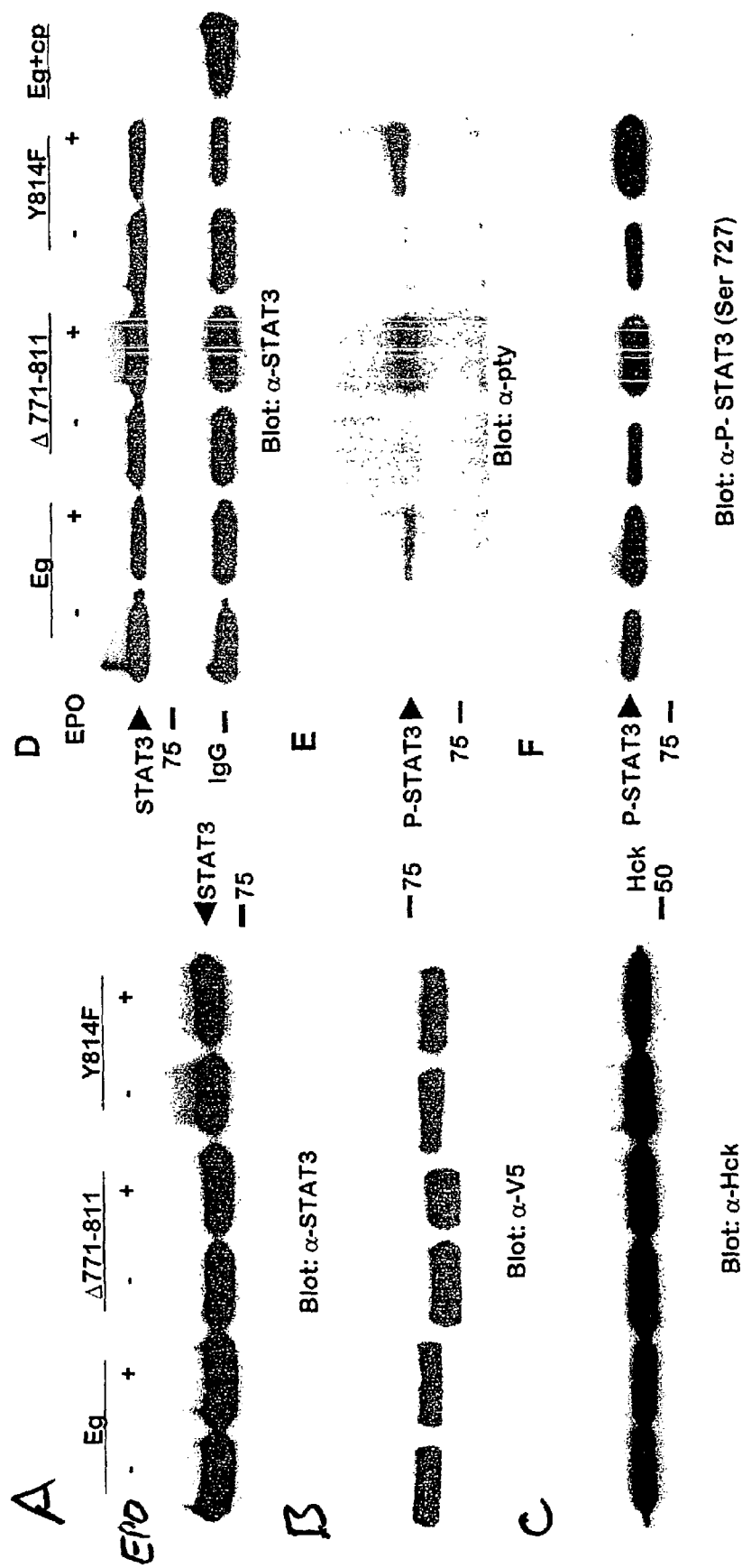
FIG. 8 is a series of blots showing that the activating phosphorylation of STAT3 is not inhibited by mutation of tyrosine residue 814 or the deletion of amino acids 771 to 811.

FIG. 8: The activating phosphorylation of STAT3 is not inhibited by mutation of tyrosine residue 814 or deletion of amino acids 771 to 811. Baf-B03 cells were transfected with cDNAs for Hck and Eg, Y814F or Δ771-811, respectively. Lysates of these cells were either left normal (−) or stimulated with 8 U/mL EPO (+). The lysates were investigated by blotting with a-STAT3 antibody (A) to detect endogenous STAT3 expression, by V5 antibodies to detect receptor constructs (B), and by α-Hck antibodies (C) to detect Hck. Afterwards, the lysates were used in precipitation experiments using α-STAT3 antibodies (right panel). To control STAT3 precipitation, aliquots of the IP reactions were incubated with α-STAT3 antibody (D), the specificity of the STAT3 antiserum was tested by preincubation of α-STAT3 with a specific blocking peptide (D, lane 7). To test for STAT3 phosphorylation, the membrane E was blotted with anti-phosphotyrosine antibody, then stripped and rebotted with an antibody against serine(727)-phosphorylated STAT3 (F).

Figure 9:
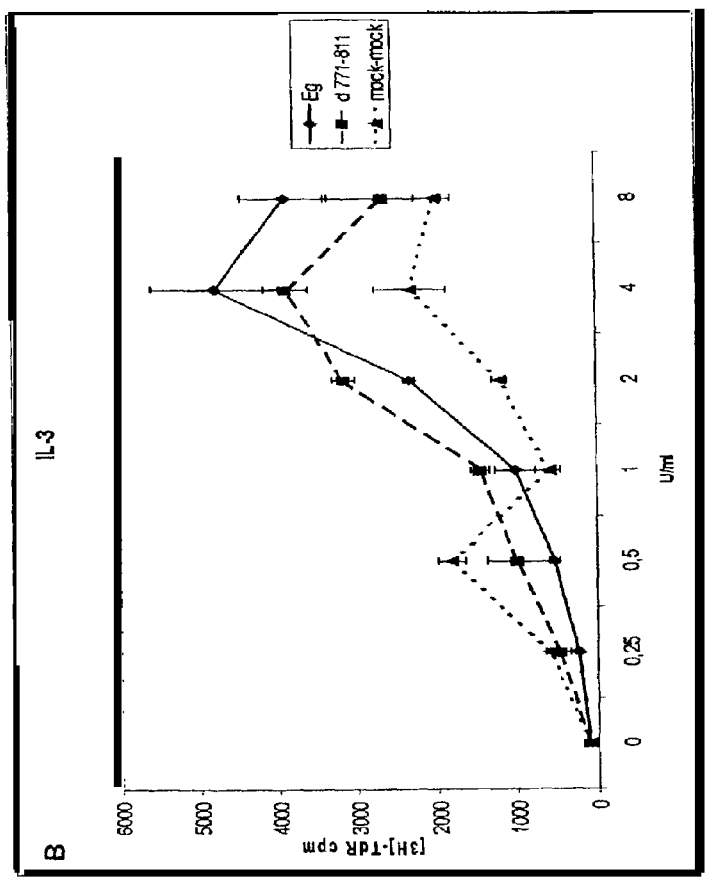
FIG. 9 is a series of blots showing that the deletion of the Hck binding site results in considerable loss of EPO-induced proliferation.
Figure 9:
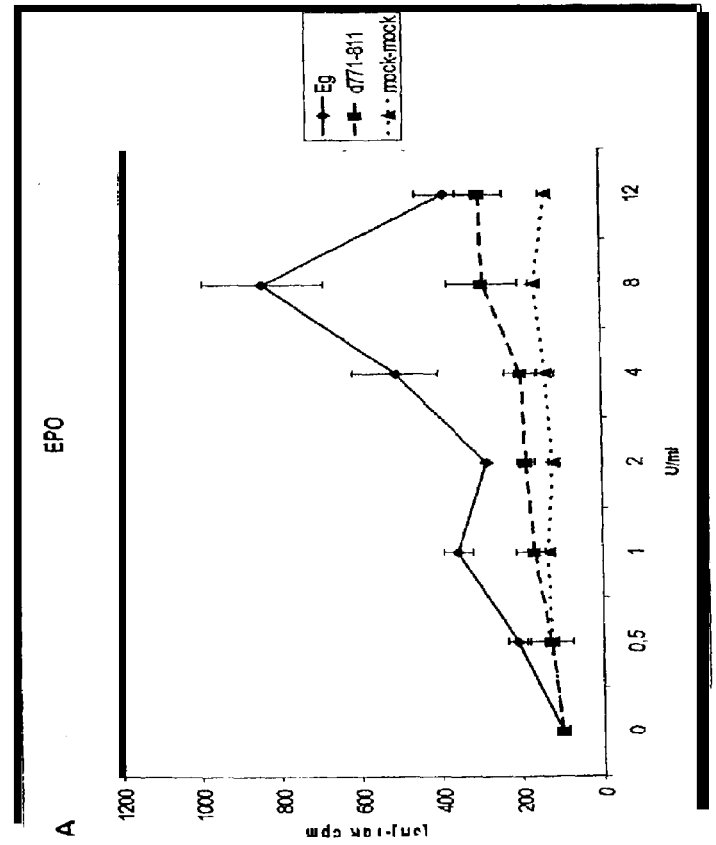

FIG. 9: Deletion of the Hck binding site results in considerable loss of EPO-induced proliferation. Clonally derived Baf-B03 cells were used for proliferation assays. Cells expressing Eg (diamonds), d771-811 (rectangles) or expression vectors alone (triangles) were grown in 96-well plates. $3 \times 10^5$ cells per well were stimulated for 48 hours by the EPO concentrations (A) or IL-3 (B) as indicated. In the last six hours, samples were labeled in triplicate by $^3$H-thymidine. After osmotic cell lysis, the incorporated radioactivity was determined using a scintillation counter. Mean values of the relative counts of three different clones were used while the standard deviation is as indicated.

Figure 10:
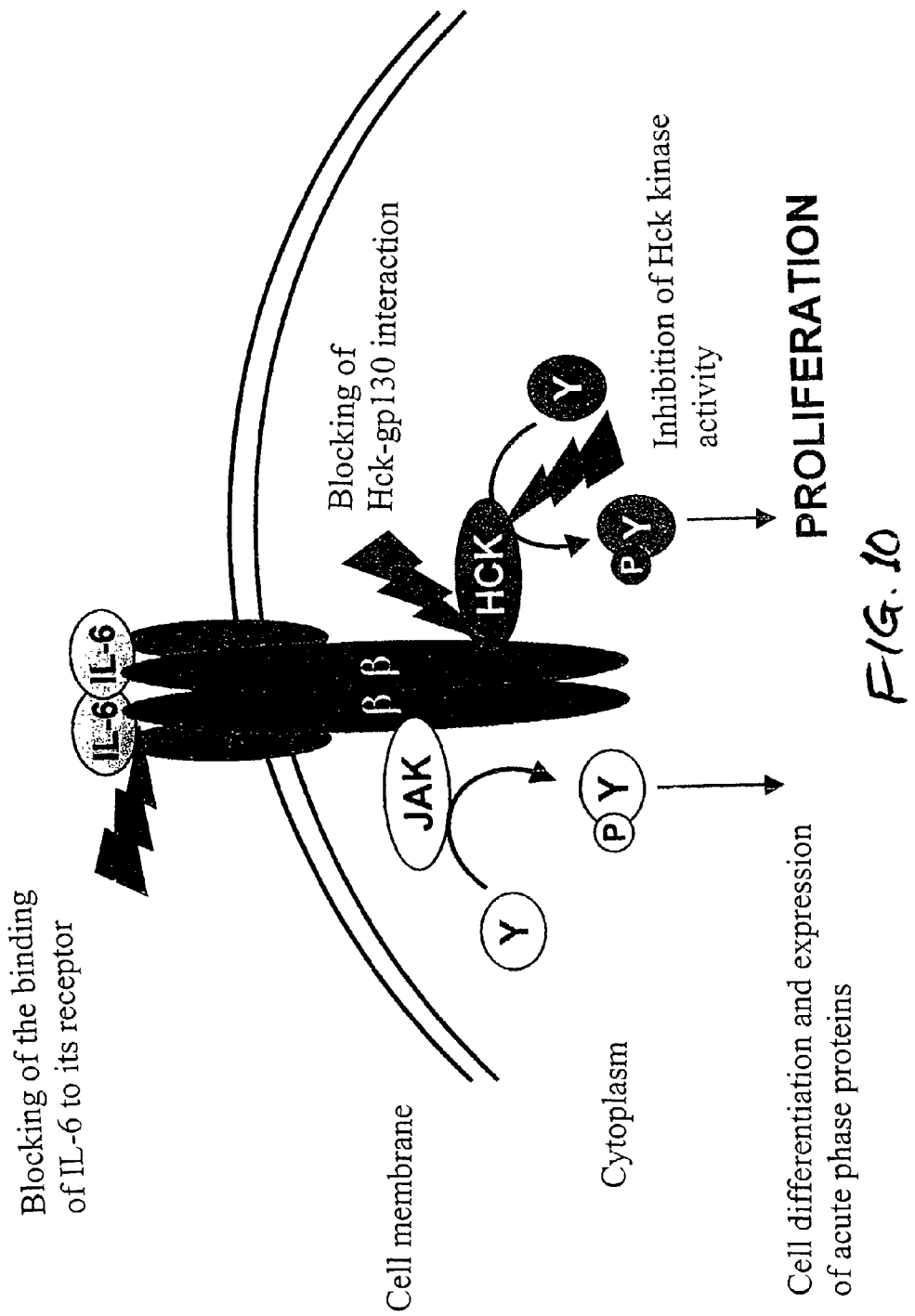
FIG. 10 is a diagram showing the mechanism for the inhibition of IL-6 signal transduction.

FIG. 10: Inhibition of IL-6 signal transduction

FIG. 11: Sequence of the sequence deleted in gp130 (SEQ ID NO:24).

To identify the gp130 binding domain for Hck several gp130 mutants were constructed. These mutants are based on a chimeric receptor comprising the extracellular portion of the erythropoietin receptor (EPOR) and the intracellular portion of human gp130. Hemmann, U., et al., "Differential activation of acute phase response factor/STAT3 and STAT1 via the cytoplasmic domain of the interleukin-6 signal transducer gp130," *J. Biol. Chem.*, 271:12999 (1996). These EPOR/gp130 chimeras enabled the study of the activation of gp130 by erythropoietin (EPO) after transfection of a single molecule. By genetically modifying these chimeric receptor constructs we identified a region of 41 amino acids (aa 771-811) located on the C-terminal side of the Box3 motif of gp130 which was necessary for Hck binding. The region is rich in negatively charged amino acids and was therefore designated "acidic domain". Unexpectedly, the internal deletion of this acidic domain significantly reduces gp130 induced proliferation to a considerable extent. The results show for the first time that the activation of a Src kinase, Hck, is mediated by an acidic domain of gp130 which is critical for the transmission of proliferative signals.

Materials and Methods

Reagents

Purified recombinant murine erythropoietin (rmEPO) was purchased from Boehringer (Mannheim, Germany), and purified murine interleukin-3 (rm IL-3) was obtained from Biosource International (Nivelles, Belgium). All reagents for cell lysis, protein extraction, sodium dodecyl sulfate-polyacrylamide gel electrophoresis (SDS-PAGE), and immunoblotting were purchased from Sigma (Munich, Germany) or Bio-Rad (Munich, Germany). Protein-A sepharose was obtained from Pharmacia Biotech (Freiburg, Germany). The purified mouse monoclonal antibodies anti-His (C-term) and anti-V5 were purchased from Invitrogen (Leek, Netherlands). The rabbit polyclonal antibody N-30 (anti-Hck), the antibody C-20 (anti STAT3), the anti-phosphotyrosine antibody PY99 and the specific blocking peptide representing amino acids 8-37 of Hck were obtained from Santa Cruz Biotechnology (Santa Cruz, Calif.). The specific antibody against serine-phosphorylated STAT3 was purchased from New England Biolabs (Schwalbach, Germany). $^3$H-Thymidine was purchased from Amersham (Braunschweig, Germany). Cell culture media and sera were obtained from Bio Witthaker (Verviers, Belgium) and Gibco (Paisley, UK). The wild type erythropoietin receptor-gp130 (Eg) fusion protein was a kind gift from Friedemann Horn (University of Leipzig, Germany). All enzymes for cloning procedures and the liposomal transfection reagent DOTAP were purchased from Boehringer (Boehringer Mannheim, Germany). The mammalian expression vectors pcDNA3, pcDNA3.1(−)/myc-His, pcDNA6/V5-His and the selection reagent blasticidin were purchased from Invitrogen (Leek, Netherlands). The expression vector pApuro was a gift from Seth Corey (Pittsburgh, Pa.). The selection reagent puromycin was obtained from Sigma (Munich, Germany).

Cloning of Eg and Mutants

Cloning of Eg

The chimeric receptor (Eg) was constructed by cloning of the extracellular domain of the mouse erythropoietin receptor to the cytoplasmic domain of human gp130 using an introduced EcoRI site as described elsewhere (Hemmann et al., *J. Biol. Chem.*, 271:12999 (1996), cited above). This construct was then cloned into pcDNA3.1/myc-His using introduced XbaI and BamHI sites and standard PCR methods.

Truncation Mutations

The C-terminal truncation mutants t828, t770, t722, t702, t685, and t650 (numbers referring to the amino acid positions of wild type human gp130) were constructed using the full length fusion protein (Eg) cloned into pcDNA3.1/myc-His as template in a single step PCR protocol. A universal sense primer, containing an integrated XbaI site and a Kozak signal sequence (5'-gggccctctagaccagccatggacaaactc-3'; SEQ ID NO:1) as well as the following truncation specific antisense primers containing an integrated BamHI site were used.

```
t828a:  atctggggatccttcatgctgactgcagttctg,
        (SEQ ID NO:2)

t770a:  gacttggactgaggatccttggtgtctgta,
        (SEQ ID NO:3)

t722a:  actgctggatccttcagtattaattttttc,
        (SEQ ID NO:4)

t702a:  ttctggggatccttttttgtcatttgcttctat,
        (SEQ ID NO:5)

t685a:  ggcaatatgactggatccaggatctggaac,
        (SEQ ID NO:6)

t650a:  atctggaacattaggggatccgtgttttttaattag.
        (SEQ ID NO:7)
```

Deletion Mutations

The deletion mutants Δ681-721, Δ771-827, Δ771-811, Δ820-827, Δ812-827, and Δ812-819 were established in a two step PCR protocol using Eg as template. In the first step the deletions were completed by partially complementary internal primers

```
(Δ681–721s:  cacaattttaattcaaaaggacacagcagtggtatt,
             (SEQ ID NO:8)

Δ681–721a:   aataccactgctgtgtccttttgaattaaaattgtg,
             (SEQ ID NO:9)

Δ771–827s:   agtggctacagacaccaaatttcacattttgaaagg,
             (SEQ ID NO:10)

Δ771–827a:   ccttcaaaatgtgaaatttggtgtctgtagccact,
             (SEQ ID NO:11)

Δ771–811s:   agtggctacagacaccaacaacagtacttcaaacag,
             (SEQ ID NO:12)

Δ771–811a:   ctgtttgaagtactgttgttggtgtctgtagccact,
             (SEQ ID NO:13)

Δ820–827s:   tacttcaaacagaactgcatttcacattttgaaagg,
             (SEQ ID NO:14)

Δ820–827a:   ccttcaaaatgtgaaatgcagttctgtttgaagta,
             (SEQ ID NO:15)

Δ812–827s:   gatggtattttgcccaggagtcagcatgaatccagt,
             (SEQ ID NO:16)

Δ812–827a:   actggattcatgctgactcctgggcaaaataccatc,
             (SEQ ID NO:17)

Δ812–819s:   gatggtattttgcccaggagtcagcatgaatccagt,
             (SEQ ID NO:18)
```

```
        -continued
Δ812–819a:   actggattcatgctgactcctgggcaaaataccatc)
             (SEQ ID NO:19))
``` and two terminal Primers binding 5' (Ecosfp: ctgaccgctagcgaattcacttttactacc; SEQ ID NO:20) and 3' (Bamafp: ggtaccgagctcggatccctgaggcatgtagcc; SEQ ID NO:21) of gp130. In the second step the two corresponding PCR products were annealed using Ecosfp and Bamafp to complete the deleted internal EcoRI-BamHI fragments. These fragments were ligated to EcoRI-BamHI-cut Eg which was inserted in pcDNA3.1 (−)/myc-His.

Point Mutations

Point mutants Y759F, Y767F, Y814F, Y905F, and Y915F were constructed as described above using a two step PCR protocol wherein specific internal oligonucleotides containing the desired mutation were used. Mutant YY759/767FF was cloned using Y767F as template in a PCR reaction with primers containing the Y759F mutation. The DDM mutant was accomplished using the YY759/767FF mutant as template in a PCR with primers Δ771-827s and Δ771-827a.

Vectors for Stable Transfection in Baf-B03 Cells

For stable transfection of receptor mutants into Baf-B03 cells, these DNAs were cloned into vector DNA6/V5-His using XbaI and ApaI as restriction enzymes.

Construction of pDpuro-Hck

Transfection vector pDpuro was constructed by fusing the promoter region and the multiple cloning site of pcDNA 3 into the pApuro backbone. This was done in a two step ligation protocol using NcoI and PvuI restriction sites. Hck cDNA was obtained from the ATCC and cloned into this vector using the EcoRI site.

Cells, Cell Culture, and Transfection

Cos-7 cells were obtained form the German collection of Microorganisms and Cell Culture (Deutsche Sammlung von Mikroorganismen and Zellkultur, DSM, Braunschweig, Germany). The IL-3-dependent murine pro B-cell line Baf-B03 was a kind gift from Dr. Mark Showers (Dana Faber Cancer Institute). Cos-7 cells were routinely grown in Dulbecco's Modified Eagles Medium (DMEM) supplemented with 10% FCS, and L-glutamine. Baf-B03 cells were cultured in RPMI-1640 supplemented with 10% FCS and 10% WEHI-3B cell-conditioned medium as a source for murine IL-3. Cos-7 cells were transiently transfected using the liposomal transfection reagent DOTAP according to the manufacturer's protocol and as described [Warmuth et al., *J. Biol. Chem*, 272:33260 (1997)]. For transient co-transfection, 50 µg fusion receptor DNA and 25 µg Hck-DNA (cloned into pcDNA3 expression vector) were used. Baf-B03 cells were stably transfected by electroporation using $1 \times 10^7$ cells and 20 µg DNA of the receptor constructs. Cells were resuspended in 800 µl PBS without calcium and magnesium (BioWitthaker, Verviers, Belgium) and electroporated using a pulse of 350 V and 950 µF. Selection of transfected cells was started 48 hrs. later by using 8 µg/ml blasticidin. After 10 days, single clones of positively transfected cells were established by limited dilution. Highly expressing single clones were electroporated with Hck cDNA (cloned into pDpuro Hck expression vector) as described above. Selection of double-transfected cells was started 48 hrs. later by 5 µg/ml puromycin and 8 µg/ml blasticidin. Generally, the cells were cultured under selection until three days prior to stimulation and lysis. At least three similarly expressing clones per mutant were cultivated for experiments.

Preparation of Cell Lysates

Prior to all experiments, cells were starved by serum deprivation for 16 to 20 hours. Cos-7 cells and Baf-B03 cells were lysed with a lysis buffer containing 0.5% NP40, 1 mM EDTA, 150 mM NaCl, 1 mM NaF, 50 mM Tris pH 7.4, 10% gycerol, 1 mM phenylmethylsulfonylfluoride, 10 µg/mL leupeptin, 10 µg/mL aprotinin, and 2 mM sodium orthovanadate. Briefly, pelleted Baf-B03 cells from 150 mL suspension (about $7 \times 10^7$ cells) were washed two times with PBS. For stimulation, the pellet was resuspended in 10 mL PBS and incubated with 8U/mL EPO under gentle shaking for 10 min at 37° C. The reaction was stopped by adding 40 mL of ice cold lysis PBS. After an additional washing step, the pellet was resuspended with 1.5 mL ice cold lysis buffer. Cos-7 cells were scraped off from the bottom of confluent 175 $cm^2$ tissue flasks after starvation, washed once with PBS and resuspended in 1.2 mL of ice cold lysis buffer.

After rotating for 25 min on an overhead rotor at 4° C., the lysates were pelleted at 14000 rpm and 4° C. for 15 min to remove insoluble material. Total protein concentration was measured using a Bradford protein assay (BioRad). Lysates were stored at −20° C. or immediately used for experiments.

Immunoprecipitation and Western Blot

Immunoprecipitation (IP), 500 µg Cos-7 cell lysate or 800 µg of Baf-B03 cell lysate were incubated with 2 µg of the appropriate antibodies from 2 hours up to 18 hrs. at 4° C. on a rotating plate. 100 µL protein-A beads were washed twice in IP-washing buffer (0.1% NP40, 1 mM EDTA, 150 mM NaCl, 1 mM NaF, 50 mM Tris pH 7.4) and then resuspended in 50 µL IP-washing buffer. 100 µL of this mixture were added to each IP reaction. Following an additional incubation for 2 hrs. at 4° C. the precipitates were each washed four times in 500 µL IP-washing buffer. After boiling in 4× sample buffer, the precipitates were pelleted and the supernatants loaded on 10% SDS gels. Peptide blocking experiments for Hck kinase and STAT3 were performed with the specific blocking peptides (Santa Cruz) according to the manufacturer's protocol. For normal expression controls of recombinant proteins, lysate containing 100 µg proteins was subjected to electrophoresis. After transfer of the proteins to Hybond-ECL nitrocellulose membranes (Amersham, Braunschweig, Germany), the membranes were blocked for 2 hours in TBST (Tris buffered saline with 0.05% Tween 20) containing 2% skim milk (Merck, Darmstadt, Germany). Following a one-minute wash in TBST, the primary antibodies diluted in TBST/1% BSA (1:1000) were incubated for 2 hours or overnight. Membranes were washed four times with TBST, and then the appropriate peroxidase-linked secondary antibody diluted in TBST/1% BSA (1:3000) was incubated for 35 minutes. After a final washing step, the proteins were detected using the Amersham ECL-system or ECL plus-system according to the manufacturer's guidelines.

Proliferation Assays

Proliferation assays were carried out in 96-well plates using $5 \times 10^3$ Baf-B03 cells per well. For all experiments the cells were washed twice with PBS and resuspended in RPMI medium supplemented only with 10% FCS. Aliquots in triplicate of monoclonal cells expressing recombinant proteins were stimulated with the indicated concentrations of EPO, or IL-3. Thereafter, the plates were incubated for 48 hours at 37° C. and pulsed with 0.5 µCi $^3$H-thymidine per well for 6 hours. After freezing for at least 2 hours at −20° C., the cells were harvested and the $^3$H-thymidine incorporation was measured using an automatic P-counter (Wallac Turku, Finland).

Results

Selective Binding of Hck to gp130

The Src family kinases Fyn, Lyn, and Hck are physically associated with gp130 in MM and embryonic stem (ES) cells (Hallek, P., et al., *Exp Hematol*, 25:1367 (1997), cited above); Ernst, M., et al., "Functional and biochemical association of Hck with the LIF/IL-6 receptor signal transducing subunit gp130 in embryonic stem cells," *EMBO*, 13:1574 (1994). However, the structural requirements for this complex formation remained unclear. The possible binding of Hck to gp130 was investigated according to the present invention. In order to identify the gp130-binding domain for Hck we generated several truncation and deletion mutants of gp130 (FIG. 1). For this purpose, we used a chimeric receptor comprising the extracellular domain of the erythropoietin receptor (EPOR) and the transmembrane and intracellular portions of gp130 (Eg). This strategy allowed us to transfect only a single chimeric receptor molecule, since the EPOR is functional as homodimer. Furthermore, when EPOR negative cells were used, effects of endogenously expressed IL-6R components could be excluded, because activation of the chimeric receptor is achieved by stimulation with EPO. In order to facilitate the detection of the chimeric receptor, all receptor mutants were tagged with poly-His peptide allowing detection by the anti-histidine antibody, anti-His-C-term. These mutants were transfected together with a wild type Hck expression plasmid, pcDNA3-Hck, into Cos-7 cells which do not express EpoR endogenously. A similar protein expression of the various receptor mutants and of Hck was obtained (FIGS. 4A and B, left panel). The double or triple bands of the different receptor mutants (FIG. 4A) could be most likely explained by differential glycosylation; however, only one of these forms seemed to co-precipitate with Hck (FIG. 4C). Lysates of double-transfected Cos-7 cells were then used for co-precipitation experiments in which anti-Hck precipitates were resolved by SDS-PAGE and then subjected to immunoblotting with anti-His antibody to detect complexes of receptor mutants with Hck (FIG. 4C). Aliquots of the IP reactions were loaded on an additional gel and blotted with the Hck antibody (N-30) to verify that similar amounts of Hck were precipitated (FIG. 4D). To evaluate the specificity of the precipitating anti-Hck antibody, blocking experiments with a specific blocking peptide (see Methods section) were also performed showing that precipitation of Hck was completely blocked by the peptide (FIGS. 4C, 4D, lanes 1). C-terminal truncation at amino acid 770 (mutant t770) resulted in a substantial loss of Hck binding (FIG. 4C, lane 5). In contrast, Hck binding remained unaffected when further C-terminal truncations of gp130 were used (mutant t828; FIG. 4C, lane 4). This suggested that a putative Hck binding domain was located between amino acids 770 and 828 of gp130. When the experiment was performed in the opposite direction, i.e., with anti-His IP followed by anti-Hck immunoblotting, a fraction of Hck remained bound unspecifically to protein A beads rendering a quantitative analysis impossible.

A C-Terminal Region of gp130 is Necessary for Hck Binding

Figure 5A:
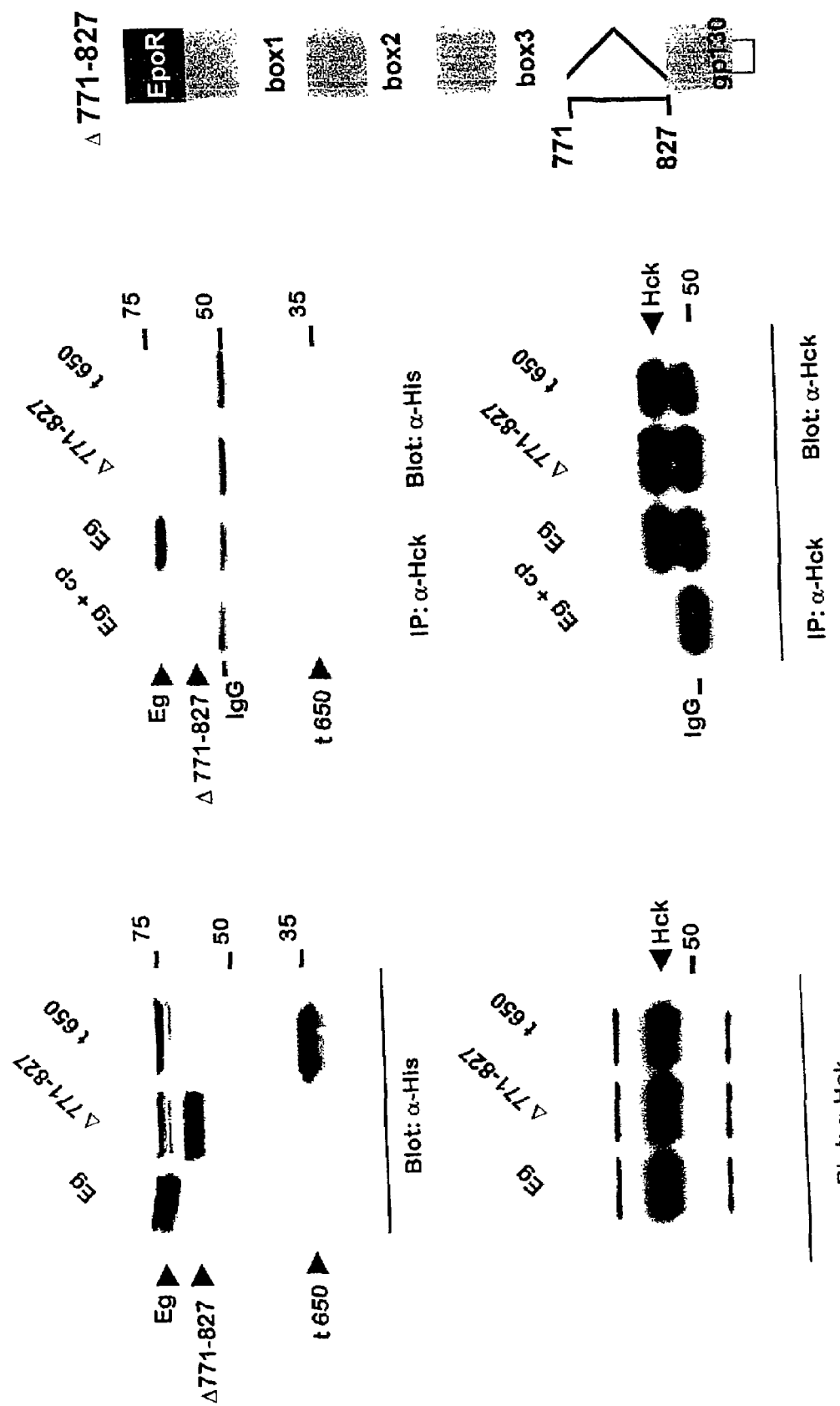
FIG. 5 is a series of western blots showing that the deletion of 41 amino acids inhibits the binding of Hck to gp130.

The binding region for Hck suggested by the above experiments included none of the homology boxes (see FIG. 1) shared amongst different growth factor receptors and shown to be important docking regions for signaling proteins (Lai, C. F., et al., "Separate signalling mechanisms are involved in the control of STAT protein activation and gene regulation via the interleukin 6 response element by the box 3 motif of gp130," *J. Bio. Chem.*, 270:14847 (1995)); Narazaki, M., et al., "Activation of JAK2 kinase mediated by the interleukin 6 signal transducer gp130," *Proc. Natl. Acad. Sci. USA*, 91:2285 (1994); Murakami, M., et al., "Critical cytoplasmic region of the interleukin 6 signal transducer gp130 is conserved in the cytokine receptor family," *Proc. Natl. Acad. Sci. USA*, 88:11349 (1991); Tanner, J. W. et al., "The conserved box 1 motif of cytokine receptors is required for association with JAK kinases," *J. Biol. Chem.*, 270:6523 (1995); Adachi, T., et al., "The mapping of the Lyn kinase binding site of the common beta subunit of IL-3/granulocyte-macrophage colony-stimulating factor/IL-5 receptor," *J. Immunol.*, 162:1496 (1999); Rao, P., "A membrane proximal domain of the human interleukin-3 receptor beta c subunit that signals DNA synthesis in NIH 3YT3 cells specifically binds a complex of Src and Janus family tyrosine kinases and phostidylinositol," *J. Biol. Chem.*, 270:6886 (1995)). However, a striking feature of the gp130 region from amino acids 770 to 828 was a remarkably high content of negatively charged amino acids. Therefore, the Hck binding region 770-828 of gp130 was termed "acidic domain." Finally, other regions containing a high fraction of negatively charged amino acids within the region from amino acid 770 to 828 were screened to search for further potential Hck binding motifs. Two such regions were found. One was the region between amino acids 771 and 827; the other was located between amino acids 681 and 721. To evaluate the role of these two "acidic domains" for Hck binding, also additional Eg mutants with internal deletions in these regions were constructed (FIG. 1). When these mutants were used to assess the binding of Hck to gp130 we observed that the Hck/gp130 association remained unchanged by internal deletion of amino acids 681 to 721 ($\Delta$681-721) (FIG. 4C, lane 3), while the internal deletion of residues 771 to 827 ($\Delta$771-827) resulted in an >90% decrease of Hck co-precipitation with gp130 in Cos-7 cells (FIG. 5A, lane 3, upper right panel). Again, controls showed-similar expression of receptor mutants and Hck (left panel) as well as similar precipitation of Hck from lysates of double-transfected Cos-7 cells (lower right panel). Also, as a negative control for Hck binding, mutant t650 bearing only 8 amino acids of the intracellular domain of gp130 was used and showed no binding to Hck (FIGS. 4C, lane 9, and 5A, upper right panel).

Hck Binds to gp130 via an Acidic Domain of 41 Amino Acids and Independently of Tyrosine Residues 759, 767, and 814

Figure 5B:
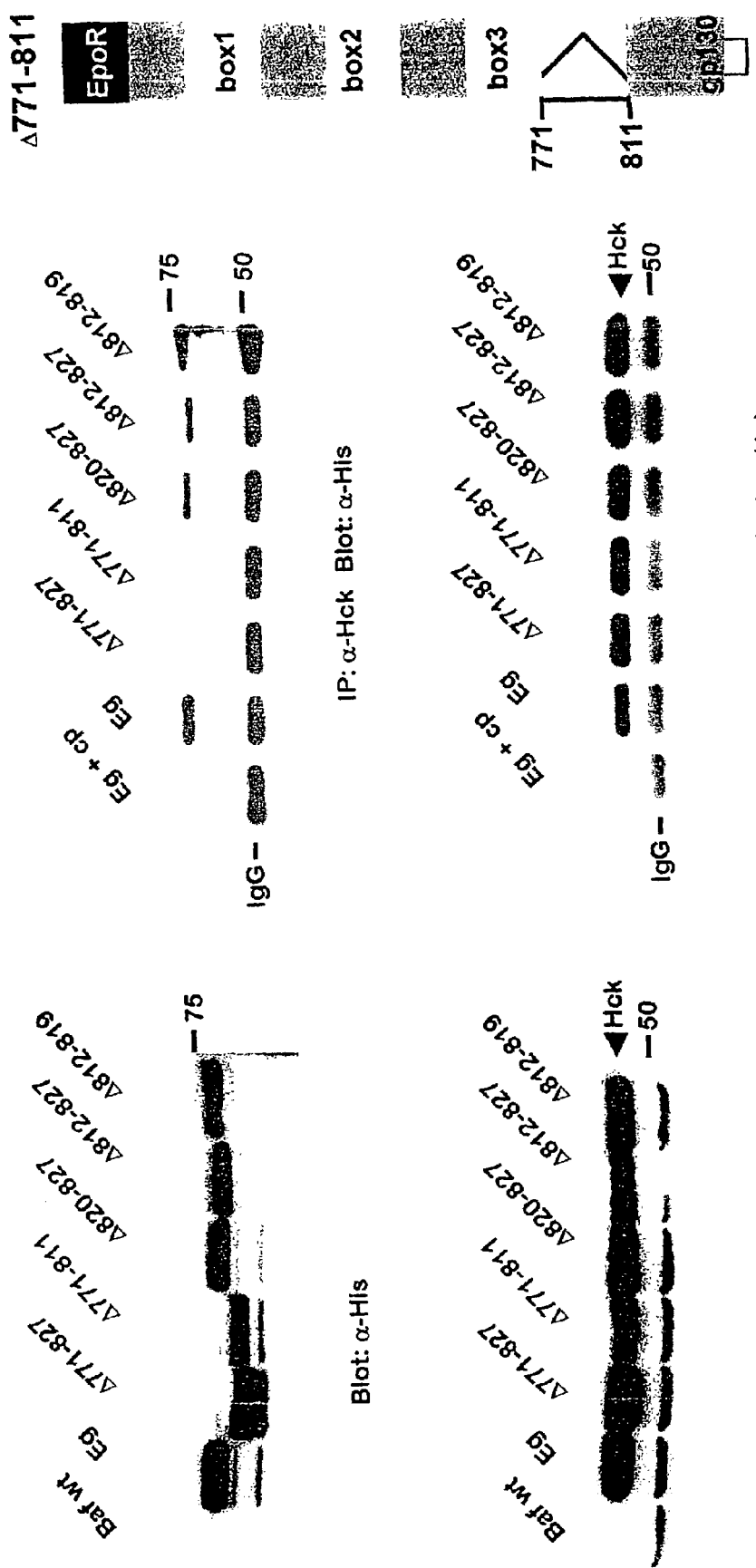

In order to define the Hck binding domain more precisely, mutants with smaller deletions were constructed (FIG. 5). The goal was to determine whether two well characterized protein binding motifs, tyrosine residues 814 and 767 (Y814 and Y767), localized within or near this putative Hck binding domain and shown to be docking sites for STAT3 (Gerhartz, et al., *J. Biol. Chem.*, 271:12991 (1996), as cited above; and Hemmann et al., *J. Biol. Chem.*, 271:12999 (1996), as cited above) interfered with Hck binding. The deletions either encompassed Y814 ($\Delta$812-827 and $\Delta$812-819) or were located either on the N-terminal ($\Delta$771-811) or C-terminal ($\Delta$820-827) side thereof. The constructs were again expressed together with a Hck expression plasmid (pDpuroHck) in Cos-7 cells (FIG. 5B, left panel). Controls were performed as indicated. In addition, lysates of non-transfected Cos-7 cells were loaded (left panel, lanes 1) to control for the expression of transfected Hck and receptor mutant cDNAs. From these cell lysates, anti-Hck precipitates were blotted with anti-His antibody to detect gp130-Hck complexes. As shown in FIG. 5B (upper right panel, lane 3), the internal deletion of amino acids 771-827 ($\Delta$771-827) resulted in a 90% loss of gp130 co-precipitation with Hck, and a complete disruption of Hck binding to gp130 occurred with mutant $\Delta$771-811 (FIG. 5B, lane 4). In marked contrast, Hck binding to mutants $\Delta$812-827 and $\Delta$812-819 was similar to wild type gp130 (lanes 6 and 7). These results suggested that the formation of the Hck-gp130 complex was independent, of the STAT3 binding at Y814 and Hck bound to gp130 at an acidic domain. This domain is located between the box 3 motif harboring docking sites for SHP-2 ($Y^{759}XXV$) (Stahl N., 1995] and STAT3 ($Y^{767}XXQ$), and another STAT3 binding motif, $Y^{814}XXQ$. In order to exclude that these binding sites participate in the interaction of gp130 with Hck, we introduced specific tyrosine-to-phenylalanine mutations at these tyrosine residues. Again, the different mutants (FIG. 3) were transfected into Cos-7 cells and used in co-immunoprecipitation experiments performed as above. The mutation of Y814 to phenylalanine resulted in no significant change in Hck-gp130 complex formation compared to wild, type gp130 (FIG. 6A, upper right panel, lanes 2 and 3). This result confirmed the conclusion that Hck binding was independent of Y814 and of STAT3 binding to this residue. FIG. 6A shows results with single point mutations of essential residues (Y759F, Y767F), a double point mutation (YY759/767FF), and a triple mutant containing Y759F, Y767F, and $\Delta$771-827 (DDM). Neither the single nor the double point mutations resulted in different co-precipitation pattern compared to wild type gp130 (upper right panel lanes, 2-5). In addition, the DDM mutant (lane 7) showed the same reduction of Hck binding to gp130 (>90%) as the single $\Delta$771-827 mutant (lane 6). Taken together, these results show that the interaction of Hck with gp130 was not mediated via the known STAT3 or SHP-2 docking sites (Y759, Y767, or Y814).

Eg Stimulation Induces Tyrosine Phosphorylation of Various Cytoplasmic Proteins in the Growth Factor Dependent Cell Line Baf-B03

To explore the functional effects of the binding of Hck to gp130 we established stable transfectants of gp130 mutants using the growth factor dependent pro B-cell line Baf-B03 (see Methods section). The functionality of the Eg receptor in these cells was tested by investigating the tyrosine phosphorylation of cytosolic proteins in response to EPO stimulation. For this purpose, Baf-B03 cells were stimulated either with 80 U/ml EPO or with medium and subsequently blotted with anti-phosphotyrosine antibody PY-99 to detect tyrosine-phosphorylated proteins. As shown in FIG. 7A, EPO induced an increase in tyrosine phosphorylation of several cytosolic proteins in Eg/Hck-transfected Baf-B03 cells. The apparent molecular weights of the most heavily tyrosine-phosphorylated proteins were: 130 kD, 120 kD, 90 kD, 75 kD, 60 kD, 58 kD, and 50 kD. This result showed that the chimeric Epo/gp130 receptor was functional in activating tyrosine kinases via gp130 in response to EPO.

The Overall Serine and Tyrosine Phosphorylation of STAT3 is not Reduced by Mutation of Y814 or Deletion of Amino Acids 771 to 811 of gp130

Since amino acids 771-811, the putative Hck binding domain, are localized in close neighborhood to tyrosine residues 767 and 814 which are STAT3 docking sites we wanted to investigate whether their deletion led to a change in STAT3 activation. It has been shown earlier that complete activation of STAT3 requires phosphorylation at tyrosine residue 705 and serine residue 727 (Wen, Z., et al., "Maximal activation of transcription of Stat1 and Stat3 requires both tyrosine and serine phosphorylation," *Cell,* 82:241 (1995); Zhang, X., et al., "Requirement of serine phosphorylation for formation of STAT-promoter complexes," *Science,* 267:1990 (1995)). To investigate the phosphorylation state of STAT3 in gp130 stimulated cells, we used the above-mentioned Baf-B03 transfectants which were stimulated by EPO: Endogenous STAT3 was precipitated from normal and EPO-stimulated transfected cell lines. (FIG. 9E). Subsequently, the immunoprecipitates were blotted with the anti-phosphotyrosine antibody PY99 and an antibody which is specific for STAT3 phosphorylated at serine 727. FIGS. 8A, 8B, and 8C demonstrate that Baf-B03 transfectants expressed endogenous STAT3 (A) as well as the transfected receptor mutants (B) and Hck (C) in similar amounts. As shown in FIGS. 8D and 8E, neither the deletion of residues 771 to 811 (lanes 3 and 4) nor the point mutation of tyrosine 814 (lanes 5 and 6) led to significant changes in STAT 3 tyrosine or serine phosphorylation when compared to cells transfected with wild type Eg and Hck (lanes 1 and 2). These results suggested that deletion of the Hck binding domain did not interfere with overall STAT3 activation. The preservation of STAT3 phosphorylation observed with the Y814F point mutant was explained by the previous observation that STAT3 specifically binds to four phosphorylated tyrosine residues of gp130, namely 767, 814, 905, and 915; therefore it seemed likely that the remaining docking motifs were able to compensate for the mutated 814 site. Additionally, the results suggested that STAT3 activation was independent from the binding of Hck to gp130 since the transfection of the mutant Δ771-811 did not cause significant changes in EPO-induced STAT3 phosphorylation.

The Deletion of the Hck Binding Domain Impairs gp130-Mediated Cell Proliferation To investigate the functional consequences of Hck-gp130 binding, we used various Baf-B03 transfectants to perform cell proliferation assays. Since Baf-B03 cells depend on IL-3 for cell growth, cells were also stimulated with this cytokin as a control. For proliferation assays, Baf-B03 cells were resuspended in IL-3-free medium and plated in 96-well plates. After two days of stimulation with the indicated amounts of EPO or IL-3, the incorporation of [$^3$H]-labeled thymidine was measured. As shown in FIG. 6A, deletion of the Hck binding domain (Δ771-811) resulted in a three- to four-fold reduction of EPO-induced proliferation compared to wild type gp130 transfected cells. However, cells expressing gp130/0771-811 still showed a two-fold increase in cell proliferation in response to EPO which could be explained by the activation of signaling intermediates different from Hck kinase. Baf-B03 cells co-transfected with the respective expression vectors alone did not proliferate upon stimulation with EPO indicating that the expression plasmids had no effect on cell proliferation. In contrast, all transfectants reacted similarly to IL-3 stimulation (FIG. 9B), thus reducing the probability that the results may be explained by the evolution of specific cell clones with altered response to growth factors. Taken together, the results suggested that the deletion of the Hck binding domain of gp130 reduced the strength of proliferative signals from gp130.

Blocking the Proliferation of IL-6 Dependent Cells

Subfragments of the previously described 41 amino acid Hck binding domain of gp130 were used to narrow down the essential parts of this domain. The subfragments, which are shown in FIG. 12, were synthesized by solid phase synthesis, N-terminally coupled to myristate in order to render them membrane soluble, and diluted in DMSO. A MM-cell line was incubated with the different peptides and cell proliferation was measured.

Figure 13:
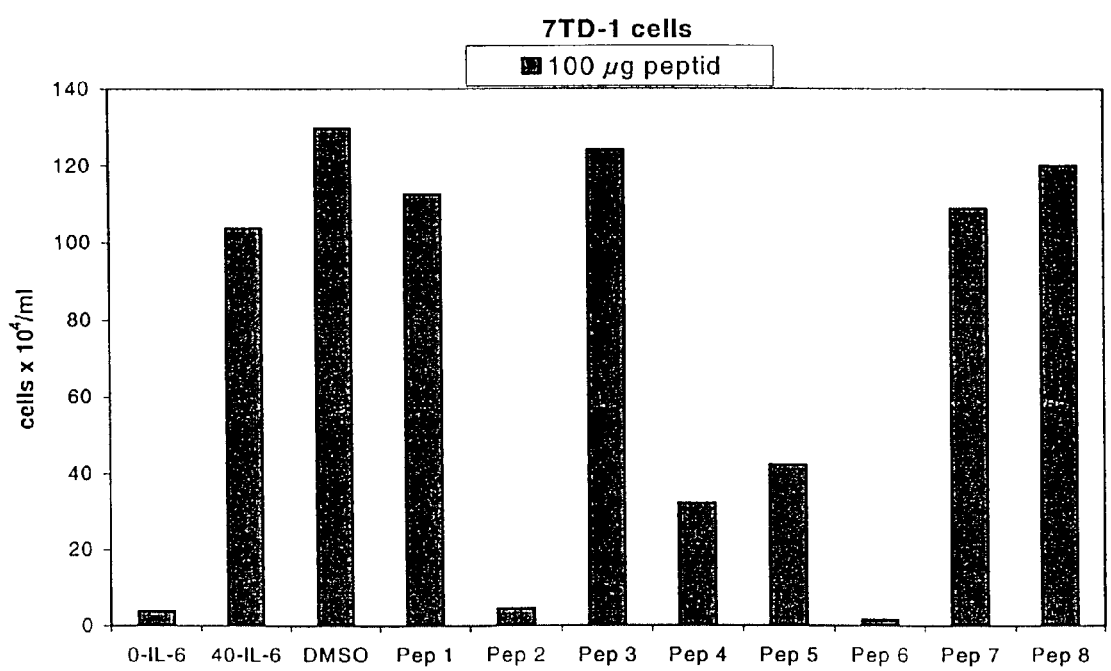
FIG. 13 is a bar graph showing the cell proliferation resulting from the use of the various peptides of FIG. 12 on a cell line stimulated with IL-6.

To determine the effects of the different peptides on IL-6 induced cell proliferation, the IL-6 dependent murine cell line 7TD-1 was stimulated with 40 pg of IL-6 and incubated with 100 μM of the different peptides. After 4 days, the cell proliferation was determined by microscopic cell counting. The results, expressed in terms of cells×10$^4$/mL, are plotted as a bar graph in FIG. 13, which indicates that cells incubated with DMSO alone (bar 3), and cells incubated with peptides 1, 3, 7 and 8 displayed proliferation similar to that of untreated cells (bar 2). Cells incubated with peptides 4 and 5 revealed an approximately 60% decrease in cell proliferation whereas cells incubated with peptides 2 and 6 reacted comparably to unstimulated cells (bar 1) and induced a down regulation of cell proliferation to the basal level.

The data indicate that the amino acid regions TQPLLD-SEERPEDLQLVD (SEQ ID NO:26) and LLDSEER-PEDLQLVD (SEQ ID NO:30) of gp130 (peptides 2 and 6) are particularly important for IL-6 induced proliferative signaling.

What is claimed is:

1. An isolated inhibitor of the binding of Hck tyrosine kinase to gp130, said inhibitor being a peptide consisting of the amino acid sequence of amino acids 771-811 of wild-type gp130, or a portion of said sequence comprising the sequence LLDSEERPEDLQLVD (SEQ ID NO:30), and said inhibitor specifically blocking the binding site of Hck to gp130.

2. A composition comprising said inhibitor of claim 1 and an excipient, wherein said inhibitor is in an amount that is effective to specifically block the binding site of Hck to gp130.

3. The composition according to claim 2 in which said inhibitor is a peptide consisting of the sequence TQPLLD-SEERPEDLQLVD (SEQ ID NO:26).

4. The composition according to claim 2 in which said inhibitor is a peptide consisting of the sequence LLDSEER-PEDLQLVD (SEQ ID NO:30).

5. An inhibitor according to claim 1 in which said inhibitor is a peptide consisting of the sequence TQPLLD-SEERPEDLQLVD (SEQ ID NO:26).

6. An inhibitor according to claim 1 in which said inhibitor is a peptide consisting of the sequence LLDSEER-PEDLQLVD (SEQ ID NO:30).

* * * * *